United States Patent [19]

Powers et al.

[11] Patent Number: 5,952,307
[45] Date of Patent: Sep. 14, 1999

[54] BASIC α-AMINOALKYLPHOSPHONATE DERIVATIVES

[75] Inventors: James C. Powers, Atlanta, Ga.; Delwin S. Jackson, Bear, Del.; Liming Ni, Little Canada, Minn.

[73] Assignee: Georgia Tech Research Corp., Atlanta, Ga.

[21] Appl. No.: 08/907,840

[22] Filed: Aug. 14, 1997

Related U.S. Application Data

[63] Continuation-in-part of application No. 08/184,286, Jan. 21, 1994, Pat. No. 5,686,419.
[51] Int. Cl.$^6$ .................................................. A61K 38/05
[52] U.S. Cl. ................................. 514/19; 514/18; 514/7; 530/331
[58] Field of Search ................................. 514/18, 19, 7; 530/331

[56] References Cited

U.S. PATENT DOCUMENTS

| | | | |
|---|---|---|---|
| 5,106,762 | 4/1992 | Bredehorst | 436/546 |
| 5,681,821 | 10/1997 | Powers | 514/19 |

OTHER PUBLICATIONS

Oleksyszyn, Biochem Biophys Res Commun 161, 143, 1989.

*Primary Examiner*—Cecilia J. Tsang
*Assistant Examiner*—David Lukton
*Attorney, Agent, or Firm*—Deveau, Colton & Marquis

[57] ABSTRACT

Peptidyl derivatives of diesters of α-aminoalkylphosphonic acids with basic substituents, their use in inhibiting serine proteases with trypsin-like specificity and their roles as anti-inflammatory agents, anticoagulants, and anti-tumor agents.

8 Claims, No Drawings

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (iii) HYPOTHETICAL: no (xi) SEQUENCE DESCRIPTION: SEQ ID NO:1:

Ala Ala Pro Met
1

(2) INFORMATION FOR SEQ ID NO:2:

(i) SEQUENCE CHARACTERISTICS:
      (A) LENGTH: 4 amino acids
      (B) TYPE: amino acid
      (D) TOPOLOGY: linear (ii) MOLECULE TYPE: peptide (iii) HYPOTHETICAL: no (xi) SEQUENCE DESCRIPTION: SEQ ID NO:2:

Lys Val Pro Val
1

(2) INFORMATION FOR SEQ ID NO:3:

(i) SEQUENCE CHARACTERISTICS:
      (A) LENGTH: 4 amino acids

```
        (B) TYPE: amino acid
        (D) TOPOLOGY: linear (ii) MOLECULE TYPE: peptide (iii) HYPOTHETICAL: no (xi) SEQUENCE DESCRIPTION: SEQ ID NO:3:

Ala Ala Pro Leu
```

BASIC α-AMINOALKYLPHOSPHONATE DERIVATIVES

This is a continuation-in-part of application Ser. No. 08/184,286 filed on Jan. 21, 1994, now U.S. Pat. No. 5,686,419.

STATEMENT OF GOVERNMENT INTEREST

This invention was made with government support under Grants No. HL34035 and HL29307 awarded by the National Heart, Lung and Blood Institute of the National Institutes of Health. The government has certain rights in the invention.

BACKGROUND OF THE INVENTION

1. Field of the Invention

This invention relates to a novel class of peptidyl derivatives of aromatic diesters of α-aminoalkylphosphonic acids useful for selectively inhibiting elastase, selectively inhibiting chymotrypsin-like enzymes and selectively inhibiting trypsin-like enzymes. The diesters of α-aminoalkylphosphonic acids are analogues of natural α-amino acids. This invention is also relates to a method for controlling tumor invasion, treating inflammation and controlling blood coagulation in patients using the novel compounds of the present invention. We have found that peptidyl derivatives of aromatic diesters of α-aminoalkylphosphonic acids are potent inhibitors of chymotrypsin-like enzymes, elastases, blood coagulation enzymes, tryptases, kaliikreins, and other serine proteases, and therefore they are useful as anti-tumor, anti-inflammatory and anticoagulant agents.

2. Description of the Related Art

Serine proteases play critical roles in several physiological processes such as digestion, blood coagulation, complement activation, fibrinolysis, and reproduction. Serine proteases are not only a physiological necessity, but also a potential hazard if they are not controlled. Blood coagulation serine proteases are responsible for vascular clotting, cerebral infarction and coronary infarction. Chymotrypsin-like enzymes and plasmin are involved in tumor invasion, tissue remodeling, and clot dissociation. Uncontrolled proteolysis by other serine proteases such as elastase may cause pancreatitis, emphysema, rheumatoid arthritis, inflammation and adult respiratory distress syndrome. Accordingly, specific and selective inhibitors of these proteases should be potent anticoagulants, anti-inflammatory agents and anti-tumor agents useful in the treatment of protease-related diseases (Powers and Harper, in *Proteinase Inhibitors*, Barrett and Salvesen, eds., Elsevier, 1986, pp. 55–152; Tryggvason, Hoyhtya and Salo, *Biochem. Biophys. Acta*, 1987, 907, 191–217, incorporated herein by reference). In vitro proteolysis by trypsin, chymotrypsin or the elastase family is a serious problem in the production, purification, isolation, transport or storage of peptides and proteins.

BRIEF SUMMARY OF THE INVENTION

It is an object of this invention to define a novel group of specific inhibitors for trypsin, elastase, chymotrypsin, granzymes, and other serine proteases. Inhibitors are compounds that can reduce or eliminate the catalytic activity of the enzyme. Trypsin and trypsin-like enzymes normally cleave peptide bonds in proteins and peptides where the amino acid residue on the carbonyl side of the split bond (P1 residue) is Lys or Arg. Elastase and elastase-like enzymes cleave peptide bonds where the P1 amino acid is Ala, Val, Ser, Leu and other similar amino acids. Chymotrypsin and chymotrypsin-like enzymes hydrolyze peptide bonds where the P1 amino acid is Trp, Tyr, Phe, Met, Leu or other amino acid residue which contain an aromatic or large alkyl side chain. All of the above enzymes have extensive secondary specificity and recognize amino acid residues removed from the P1 residue.

It is a further object of this invention to define new protease inhibitors, especially inhibitors for chymotrypsin and chymotrypsin-like enzymes, elastase inhibitors, blood coagulation enzyme inhibitors, granzyme inhibitors, and tryptase inhibitors. These inhibitors are useful for controlling tumor invasion, blood coagulation and various inflammatory conditions mediated by serine proteases. The inhibitors of this invention would be useful for treating diseases such as vascular clotting, inflammations, tumor invasion, pancreatitis, emphysema or infantile and adult respiratory distress syndrome. The inhibitors of this invention would also be useful for controlling hormone processing by serine proteases and for treating diseases related to tryptases such as inflammation and skin blistering.

It is yet another object of this invention to define a novel group of specific inhibitors useful in vitro for inhibiting trypsin, elastase, chymotrypsin and other serine proteases of similar specificity. Such inhibitors could be used to identify new proteolytic enzymes encountered in research. They could also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, tissue extracts or other proteins and peptides which are widely sold for use in clinical analyses, biomedical research, and for many other reasons.

These and other objects are accomplished by the present invention which defines novel peptidyl derivative of aryl diesters of α-aminoalkylphosphonic acids. These phosphonate derivatives are potent inhibitors of serine proteases including chymotrypsin-like enzymes, trypsin-like enzymes, elastase-like enzymes, and other enzymes with other substrate specificities. The phosophonates are stable in buffer or plamsa, and inhibit the serine proteases to give stable inhibited enzyme derivatives. The phosphonates can be used both in vitro and in vivo.

DETAILED DESCRIPTION OF THE INVENTION

Peptidyl derivatives of aryl diesters of α-aminoalkylphosphonic acids have be found to be excellent inhibitors of several serine proteases including bovine thrombin, human factor XIIa, human factor Xa, human plasma kallikrein, bovine trypsin, rat skin tryptase, human leukocyte elastase, porcine pancreatic elastase, bovine chymotrypsin, human leukocyte cathepsin G, rat mast cell protease II, mast cell tryptase, granzyme A, and granzyme K. The diesters of α-aminoalkylphosphonic acids are analogues of natural α-amino acids and are designated by the generally accepted the letter abbreviations for the amino acid followed by the superscript P. For example diphenyl α-(N-benzyloxycarbonylanino)ethylphosphonate which is related to alanine is abbreviated as Cbz-Ala$^P$(OPh)$_2$.

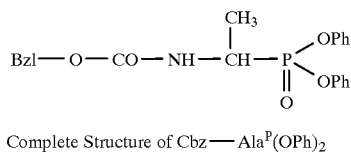

Complete Structure of Cbz—Ala$^P$(OPh)$_2$

Peptidyl derivatives of aryl diesters of α-aminoalkylphosphonic acids inhibit serine proteases by reaction with the active site serine to form "phosphonylated" enzymes, which due to similarity of phosphorus atom to the tetrahedral intermediate formed during peptide hydrolysis, show remarkable stability. The enzyme catalytic apparatus is required to activate the phosphorus atom for nucleophilic substitution and reaction with enzyme. The activation is mainly due to precise interaction with the $S_1$ pocket of various serine proteases. The following figure shows the reaction course of a phosphonate with a serine protease. The phosphonate first binds to the enzyme (below left) and then reacts to form a covalent bond with the active site serine residue (below right). Slow aging can take place with loss of the phenoxy group (below center).

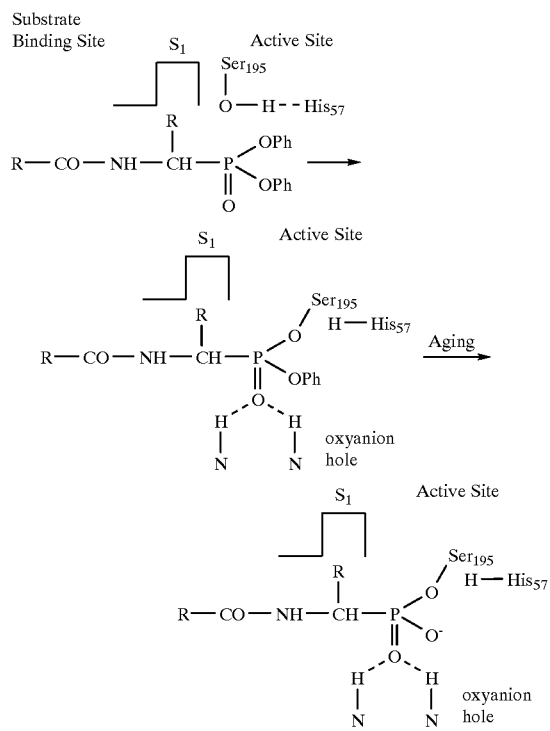

Peptides with a C-terminal phosphonate residue which is an analog of valine {e.g. Val$^P$(OPh)$_2$} are potent and specific irreversible inhibitors of elastase and elastase-like enzymes. The peptides with C-terminal phosphonate residues related to phenylalanine, other aromatic amino acids or amino acids with long aliphatic side chains are potent and specific inhibitors of chymotrypsin and chymotrypsin-like enzymes. The peptides with C-terminal phosphonate residues related to ornithine, lysine, arginine or containing a C-terminal diphenyl ester of 1-amino-1-(4-amidinophenyl) methanephosphonate {(4-AmPhGly)$^P$(OPh)$_2$} or 1-amino-1-(4-amidinophenylmethyl)methanephosphonate {(4-AmPhe)$^P$(OPh)$_2$} are specific and potent inhibitors of trypsin and trypsin-like enzymes.

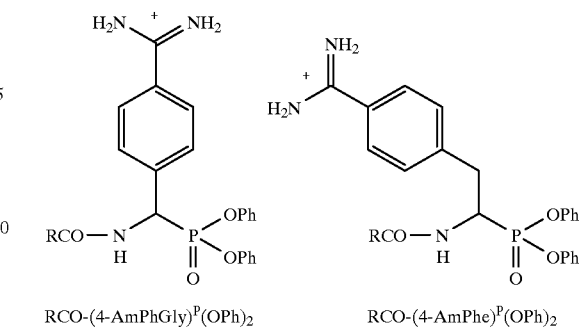

RCO-(4-AmPhGly)$^P$(OPh)$_2$    RCO-(4-AmPhe)$^P$(OPh)$_2$

Additional specificity as well as increased activation toward reaction with the enzyme can be introduced into the inhibitor molecule by variation of the amino acid sequence in the peptide portion of the structure. In fact there is a good agreement between the sequence of enzyme substrates such as a peptidyl p-nitroanilides and the sequence of an effective peptidyl phosphonate inhibitor. The best inhibitors have the sequence of the best peptidyl p-nitroanilide substrate for a particular enzyme. For example, the best inhibitor for chymotrypsin and chymotrypsin-like enzymes is Suc-Val-Pro-Phe$^P$(OPh)$_2$ which has an amino acid sequence that is analogous to Suc-Val-Pro-Phe-NA, an excellent substrate for these enzymes. With human leukocyte elastase, the two best inhibitors {MeO-Suc-Ala-Ala-Pro-Val$^P$(OPh)$_2$ and Boc-Val-Pro-Val$^P$(OPh)$_2$} have an amino acid sequence similar to MeO-Suc-Ala-Ala-Pro-Val-NA and Boc-Val-Pro-Val-NA, two excellent substrates for this enzyme. For bovine thrombin, the best phosphonate inhibitor is diphenyl Boc-D-Phe-Pro-amino(4-amidinophenyl) methanephosphonate hydrochloride, which corresponds to Boc-D-Phe-Pro-Arg-NA, which is excellent substrate for thrombin, and D-Phe-Pro-Arg-H which is an excellent peptide aldehyde inhibitor of thrombin and an anticoagulant (Bajusz, S., Szell, E., Bagdy, D., Barabas, E., Horvath, G., Dioszegi, M., Fittler, Z., Szabo, G., Juhasz, A., Tomori, E., and Szilagyi, G., *J. Med. Chem.* 33, 1729–1735 (1990) incorporated by reference). Since good substrate sequences are known in the literature for other serine proteases, it is possible to predict the structure of additional excellent phosphonate inhibitors for these enzymes {*Mammalian Proteases, A Glossary and Bibliography, Vol. 1 Endopeptidases,* Academic Press, Barrett, A. J., and McDonald, J. K. eds, pp. 1–416, 1980; *Mammalian Proteases, A Glossary and Bibliography, Vol. 2 Exopeptidases,* Academic Press, Barrett, A. J., and McDonald, J. K. eds, pp. 1–357, 1986; Lottenberg, R., Christensen, U., Jackson, C. M., and Coleman, P. L., *Methods in Enzymology* 80, 341–361 (1981) the preceding articles are incorporated herein by reference}. It is also possible to design good phosophonate inhibitors for serine proteases based on the peptide sequences found in other potent reversible and irreversible inhibitors for those same serine proteases reported in the literature {Powers and Harper, in *Proteinase Inhibitors,* Barrett and Salvesen, eds., Elsevier, 1986, pp. 55–152; Trainor, D. A., *Trends in Pharm. Sci.* 8, 303–307 (1987) the preceding articles are incorporated herein by reference}.

Examples of phosphonate inhibitors for various enzymes are given below:

| | |
|---|---|
| Cbz-Gly-Leu-Phe$^P$(OZ)(Z$^1$) | for cathepsin G and RMCP II |
| MeO-Suc-Ala-Ala-Pro-Met$^P$(OZ)(Z$^1$)(SEQ ID NO: 1) | for Cathepsin G |
| Suc-Pro-Leu-Phe$^P$(OZ)(Z$^1$) and Boc-Ala-AlaPhe$^P$(OZ)(Z$^1$) | for RMCP I |
| Boc-Gly-Leu-Phe$^P$(OZ)(Z$^1$), Suc-Phe-Leu-Phe$^P$(OZ)(Z$^1$) | for human and dog skin chymase |
| Boc-Ala-Ala-Glu$^P$(OZ)(Z$^1$) | for *S. aureus* V-8 protease |
| Cbz-Gly-Gly-Pro$^P$(OZ)(Z$^1$) | for human prolyl endopeptidase |
| Ala-Pro$^P$(OZ)(Z$^1$) | for DPP IV |
| Suc-Ala-Ala-Pro-Val$^P$(OZ)(Z$^1$)(SEQ ID NO: 2) | for PPE |
| Suc-Lys(Cbz)-Val-Pro-Val$^P$(OZ)(Z$^1$), adamantyl-SO$_2$- Lys-(COCH$_2$CH$_2$CO$_2$H)-Ala-Val$^P$(OZ)(Z$^1$), adamantyl-CH$_2$CH$_2$OCO-Glu(O-t-Bu)-Pro-Val$^P$(OZ)(Z$^1$), adamantyl-SO$_2$-Lys(CO-C$_6$H$_4$CO$_2$H)-Ala-Val$^P$(OZ)(Z$^1$) | for human leukocyte (neutrophil) elastase |
| Suc-Ala-Ala-Pro-Leu$^P$(OZ)(Z$^1$)(SEQ ID NO: 3) | for elastolytic proteinase from "Schistosoma mansoni" |
| Glu-Phe-X and Dns-Ala-Phe-X | for plasmin |
| D-Val-Gly-X and Dns-Glu-Gly-X | for factor Xa |
| Cbz-Phe-X and Cbz-Trp-X | for procine pancreatic and human plasma kallikreins |
| Cbz-Lys-X | for human skin tryptase |
| Cbz-Gly-X | for human lung tryptase |
| Cbz-Ile-Ala-Gly-X | for factors IXa, Xa, XIa, XIIa and bovine plasma kallikrein |
| Glu-Gly-X | for urokinase |
| Dns-Phe-Pro-X | for plasminogen activator |
| Dns-Ile-Pro-X | for activated protein C |
| Cbz-Trp-X | for bovine factor IXa |
| Cbz-Gly-X | for bovine factor Xa and XIa |
| Cbz-Phe-X | for bovine factor XIIa |
| Cbz-Phe-Gly-X | for trypsin | where Z represents an aryl group, a substituted aryl group or a highly fluorinated alkyl group, and Z$^1$ represents perfluoroalkoxy, a substituted aryloxy group, alkoxy, or halogen, and X represents Arg$^P$(OZ)(Z$^1$), Orn$^P$(OZ)(Z$^1$), Lys$^P$(OZ)(Z$^1$), an aryl diester of α-amino-α-(4-amidinophenyl)methanephosphonate { abbreviated NH$_2$-CH(AmPh)PO(OZ)(Z$^1$) or 4-AmPhGly$^P$(OZ)(Z$^1$)}, or 1-amino-1-(4-amidinophenylmethyl)methanephosphonate {abbreviated NH$_2$-CH(AmPhCH$_2$)PO(OZ)(Z$^1$) or 4-AmPhe$^P$(OZ)(Z$^1$)}.

The inhibitory potency of peptidyl derivatives of aryl diesters of α-aminoalkylphosphonic acids is also determined by the electronic property of the Z group. More electron withdrawing groups such as nitro, cyano, halogen, etc. on the aryl ring can make the phosphorus atom in the inhibitor more electrophilic and accelerate reaction with the active site serine of the serine protease. Reactivity toward serine proteases can also be obtained by using derivatives where the Z groups are highly fluorinated alkyl groups. However increased reactivity can also result in low chemical stability and in extreme cases, compounds may be too hydrolytically unstable for practical purposes if the Z group is too electronegative. Phosphonates where the Z group is not sufficiently electron withdrawing will be chemically very stable and will react very slowly with serine proteases or not at all. Such non-reactive inhibitors would include derivatives where OZ and Z$^1$ are simple alkoxy groups (e.g. peptidyl derivatives of alkyl diesters of α-aminoalkylphosphonic acids). Thus the phosphonate ester groups (Z) should represent a balance between these two competing factors and we find that diphenyl esters (Z=Ph, Z$^1$=OPh) are one way to obtain a balance between increased reactivity and stability in solution.

The Z$^1$ group can be replaced by either a halide or a C$_{1-6}$ alkoxy and still retain inhibitory potency. The alkoxy derivatives tend to be less reactive while the halide derivatives are more reactive with serine proteases.

Diphenyl esters of α-aminoalkylphosphonate can be synthesized by a previously described method (Oleksyszyn et al., 1979, Synthesis, 985 incorporated by reference). Di(substituted phenyl)esters of α-aminoalkylphosphonate can also be prepared by the same procedure using tris (substituted phenyl) phosphite instead of triphenyl phosphite. Perfluoroallyl diesters can be synthesized by a method involving transesterification (Szewczyk et al., Synthesis, 1982, 409–414 incorporated by reference). Alternatively, the synthesis of diesters of α-aminoalkylphosphonic acids and their peptides can be performed by esterification of the phosphonic acid moiety as described previously (Bartlett et al., Bioorg. Chem., 1986, 14, 356–377 incorporated by reference).

Monoalkyl monophenyl ester derivatives such as RCO-AA$^P$(OPh)(OEt) can be prepared by tranesterification (example 29) from RCO-AA$^P$(OPh)$_2$. Halide derivatives can be prepared by hydrolysis of the diphenyl esters RCO-AA$^P$(OPh)$_2$ to the monoester RCO-AA$^P$(OPh)(OH) (example 30). This can be converted to the chloride RCO-AA$^P$(OPh)(Cl)by reaction with thionyl chloride and other similar reagents. Reaction with KF would give the fluoride.

The synthesis of AmPhGly$^P$(OPh)$_2$ derivatives is illustrated in the following figure.

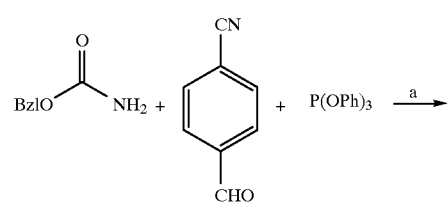

-continued

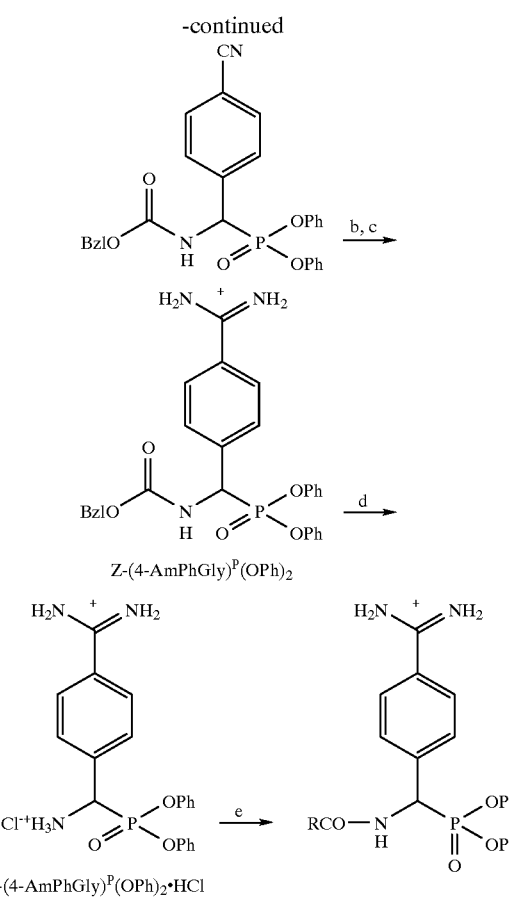

<sup>a</sup>Reagents: (a) AcOH, 60–90° C., 2h; (b) dry HCl in CHCl₃/ethonol; (c) dry NH₃ in CH₃OH; (d) 2N HCl in CH₃OH, Pd/C; (e) RCOOH, CDI Peptide derivatives of 4-amidinophenylglycine phosphonate diphenyl ester were prepared using the reactions outline in scheme shown above. The parent compound Z-(4-AmPhGly)$^P$(OPh)$_2$ was prepared by α-amidoalkylation of triphenyl phosphite with 4-cyanobenzaldehyde and benzyl carbamate (60–90° C., AcOH, 2 h) to give Z-(4-CN-PhGly)$^P$(OPh)$_2$ (70%) which was converted to the iminoester (dry HCl in CHCl₃/ethanol) and then to the amidine derivative Z-(4-AmPhGly)$^P$(OPh)$_2$ (dry NH₃ in methanol, 70–80%). Hydrogenolysis of Z-(4-AmPhGly)$^P$(OPh)$_2$ gave H-(4-AmPhGly)$^P$(OPh)$_2$ (60–80%) which was then coupled respectively with Z-Pro-OH, Boc-D-Phe-Pro-OH, and 2-NpSO$_2$-Gly-OH using CDI to give Z-Pro-(4-AmPhGly)$^P$(OPh)$_2$, Boc-D-Phe-Pro-(4-AmPhGly)$^P$(OPh)$_2$ (29%) and 2-NpSO$_2$-Gly-(4-AmPhGly)$^P$(OPh)$_2$ (30%). Deblocking gave D-Phe-Pro-(4-AmPhGly)$^P$(OPh)$_2$ (24%). The 4-amidinophenylalanine phosphonate diphenyl ester derivative Z-(4-AmPhe)$^P$(OPh)$_2$ was synthesized from 4-cyanophenylacetaldehyde using the same reaction scheme with slightly modified conditions (α-amidoalkylation, 25–35%; amidination sequence, 50–70%). Hydrogenolysis produced H-(4-ArnPhe)$^P$(OPh)$_2$ (85–90%) which was coupled with Boc-D-Phe-Pro-OH to give Boc-D-Phe-Pro-(4-AmPhe)$^P$(OPh)$_2$ (59%). Z-Pro-(4-AmPhe)$^P$(OPh)$_2$ was obtained as a transesterification product during the amidination of Z-Pro-(4-CN-Phe)$^P$(OPh)$_2$ (50%). Deblocking of with dry HCl/CHCl₃ produced D-Phe-Pro-(4-AmPhe)$^P$(OPh)$_2$ (80%).

The diphenyl phosphonate moiety is very resistant to chemical hydrolysis and at pH 7.5 we did not observe any hydrolysis after several days (monitored by $^{31}$P NMR). Furthermore, they show excellent stability in human plasma. For example Suc-Val-Pro-Phe$^P$(OPh)$_2$ has a hydrolysis half-time in human plasma of about 20 hrs. These experiments demonstrate that the phosphonate inhibitors are remarkably stable in buffer and plasma. Thus they can be used under a variety of conditions. Phosphonates have the additional advantage of being very stable in plasma and will have a high effectiveness in vivo due to their long lifetimes. Additionally, the inhibitor-enzyme complex is very stable and the enzyme did not regain any activity after several hours in the case of chymotrypsin and after several days no recovery of activity was observed in the cases of elastases and trypsin. These experiments show that it is possible to decrease or eliminate the enzyme activity and biological function of serine proteases for extended time periods.

Either racemic mixtures of the diphenyl α-aminoalkylphosphonate residue or pure diastereomers can be used in the inhibitor structures. The racemic compounds are more easily synthesized and are obtained from less expensive starting materials. The pure optically active α-aminoalkylphosphonate derivatives required in the synthesis are more difficult to synthesize (Kafarski et al., Can. J. Chem. 1983, 61, 2425) and require more expensive starting materials. In the case of the peptidyl phosphonate inhibitors which are mixtures of two diastereomers, only one will usually react with the enzymes. The pure diastereomers will possess higher inhibition rates and could be used at lower concentrations.

Peptidyl derivatives of aryl diesters of α-aminoalkylphosphonates may be used in vivo to treat diseases resulting from abnormal or uncontrolled blood coagulation or diseases caused by uncontrolled proteolysis by elastase, chymotrypsin, trypsin and related serine proteases. These inhibitors may be used in vitro to prevent proteolysis which occurs in the process of the production, isolation, purification, storage or transport of peptides and proteins.

The novel peptidyl derivatives of aryl diesters α-aminoalkylphosphonates of the present invention have the following structural formula:

A compound of the formula:

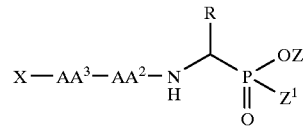

or a pharmaceutically acceptable salt, wherein:

R is selected from the group consisting of phenyl substituted with B, benzyl substituted with B on the phenyl ring, and $C_{1-6}$ alkyl substituted with B, B is selected from the group consisting of amidino {—C(═NH)NH$_2$}, guanidino {—NH—C(═NH)NH$_2$}, isothiureido {—S—C(═NH)NH$_2$}, and amino, Z is selected from the group consisting of $C_{1-6}$ perfluoroalkyl, phenyl, phenyl substituted with J, phenyl disubstituted with J, and phenyl trisubstituted with J, $Z^1$ is selected from the group consisting of $C_{1-6}$ perfluoroalkoxy, phenoxy, phenoxy substituted with J, phenoxy disubstituted with J, phenoxy trisubstituted with J, $C_{1-6}$ alkoxy, and halogen, J is selected from the group consisting of halogen, $C_{1-6}$ alkyl, $C_{1-6}$ perfluoroalkyl, $C_{1-6}$ alkoxy, $NO_2$, CN, OH, $CO_2H$, amino, $C_{1-6}$ alkylarino, $C_{2-12}$ dialkylamino, $C_{1-6}$ acyl, $C_{1-6}$ alkoxy-CO—, and $C_{1-6}$ alkyl-S—, AA³ and AA² are the same or different and are selected from the group consisting of
(a) a single bond, and
(b) a blocked or unblocked amino acid residue with the L or D configuration at the α-carbon selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, norleucine, norvaline, alpha-aminobutyric acid, citrulline, hydroxyproline, ornithine, homolysine, and homoarginine, and
(c) glycine, sarcosine, epsilon-aminocaproic acid, and beta-alanine, X is selected from the group consisting of Y—C— and Y—$SO_2$—, Y is selected from the group consisting of
(a) $C_6H_5$—CH=CH—, (2-furyl)-CH=CH—, (2-thienyl)-CH=CH—, and (2-pyridyl)—CH=CH—,
(b) $C_{1-6}$ alkenyl substituted with a heterocyclic group,
(c) $C_{1-6}$ alkenyl substituted with the group consisting of phenyl, phenyl substituted with K, phenyl disubstituted with K, phenyl trisubstituted with K, naphthyl, naphthyl substituted with K, naphthyl disubstituted with K, and naphthyl trisubstituted with K,
(d) 2-phenoxyphenyl and 3-phenoxyphenyl,
(e) Phenyl substituted with the group consisting of phenoxy, phenoxy substituted with K, phenoxy disubstituted with K, phenoxy trisubstituted with K, naphthyloxy, naphthyloxy substituted with K, naphthyloxy disubstituted with K, and naphthyloxy trisubstituted with K, and K is selected from the group consisting of halogen, $C_{1-6}$ alkyl, $C_{1-6}$ perfluoroalkyl, $C_{1-6}$ alkoxy, $NO_2$, CN, OH, $CO_2H$, amino, $C_{1-6}$ alkylamino, $C_{2-12}$ dialkylamino, $C_{1-6}$ acyl, $C_{1-6}$ alkoxy-CO—, and $C_{1-6}$ alkyl-S—.

The blocking groups which may be present on —HN—CH(R)—P(O)— or on the amino acids AA³ and AA² are those well known in the art of peptide synthesis. For example, a listing of suitable peptide blocking groups is found in Gross et al., eds. *The Peptides*, Vol. 3 (Academic Press, New York, 1981). The particular choice of the blocking group used in the compounds of the invention depends on several factors, including the blocking group's affect on enzyme specificity, its affect on phosphonate solubility, and its utility during synthesis. Suitable blocking groups include but are not limited to carbobenzyloxy (Cbz), benzoyl, t-butyloxycarbonyl (Boc), glutaryl, p-tolylsulfonyl (Tos), methoxysuccinyl (MeO-Suc), and succinyl.

The —HN—CH(R)—P(O)— residue is derived from a blocked or unblocked alpha amino acid residue —HN—CH(R)—CO— whose alpha carbonyl group has been replaced by a P(O) group. The R group is the side chain of the alpha amino acid. The alpha amino acid residue is derived from natural alpha amino acids such as those listed in the IUPAC-IUB Joint Commission on Biochemical Nomenclature report on the Nomenclature and Symbolism for Amino Acids and Peptides (J. Biol Chem., 260, 14–42 (1985) incorporated by reference). The choice of the particular amino acid residue used in the design of the phosphonate inhibitor will depend on the enzyme targeted for inhibition. For example, with chymotrypsin-like enzymes which prefer Trp, Tyr, or Phe at the P1 position of their substrates, -$Trp^P$-, -$Tyr^P$-, and -$Phe^P$- residues would be suitable phosphonate residues to incorporate into the P1 position of an inhibitor.

With elastase-like enzymes which prefer Val, Ser, or Ala at the P1 position of their substrates, -$Val^P$-, -$Ser^P$-, and -$Ala^P$- residues would be suitable phosphonate residues to incorporate in the P1 position of an inhibitor. Likewise with trypsin-like enzyme -$Lys^P$- or -$Arg^P$- residues would be suitable. Unnatural blocked or unblocked alpha amino acid residues can also be used in the design of phosphonate inhibitors. If the target serine protease will hydrolyze a substrate containing the unnatural amino acid residue at the P1 position or if an inhibitor structure contains the unnatural amino acid residue as the P1 residue, then this residue can be used in the design of a phosphonate inhibitor. For example, chymotrypsin hydrolyzes para-fluorophenylalanine containing substrates and thus the —HN—CH($CH_2C_6H_4F$)—P(O)— would be suitable for incorporating into a chymotrypsin inhibitor. Likewise, trypsin will hydrolyze substrates with aminoethylcysteine residues and cathespin G will hydrolyze aminopropylcysteine residues and thus —HN—CH($CH_2SCH_2CH_2NH_2$)—P(O)— and —HN—CH($CH_2SCH_2CH_2NH_2$)—P(O)— would respectively be suitable residues to incorporate into inhibitors for trypsin and cathepsin G. One skilled in the art of designing inhibitors for proteolytic enzyme can list many other unnatural amino acid residues which could be used in the design of suitable inhibitors.

Other aryl diesters of α-aminoalkylphosphonic acids have been prepared earlier for other purposes (illustrative examples: Oleksyszyn, J. et al., Synthesis, 1979, 985–986; Vo-Quang, Y. et al., J. Med. Chem. 1986, 43, 579–581; Kafarski, P. et al., Tetrahedron, 1987, 43, 799–803; Szewczyk, J. et al., Synthesis, 1982, 409–414; the preceding articles are incorporated herein by reference).

A few other derivatives of α-aminoalkylphosphonic acids have been prepared recently for inhibition of serine proteases, but they are not peptidyl derivatives or are peptidyl derivatives with the phosphonic acid moiety inside the peptide chain (Bartlett et al., Bioorg. Chem., 1986, 14, 356–377.; Lamden et al., Biochem. Biophys. Res. Commun., 1983, 112, 1085–1090; the preceding articles are incorporated herein by reference). We have published some of our work in a paper "Irreversible Inhibition of Serine Proteases by Peptidyl Derivatives of α-Aminoalkylphosphonate Diphenyl Esters", Oleksyszyn and Powers, *Biochem. Biophys. Res. Commun.* 161, 143–149 (May 30, 1989 issue). Subsequently, Fastrez et al., *Tetrahedron Lett.*, 1989, 30, 6861–6864 reported phosphonate inhibitors similar to those which we reported and which we describe in this specification (both the preceding articles are incorporated herein by reference). Many other examples are given in the tables.

The following compounds are representative of but do not limit the invention:

Diphenyl amino(4-amidinophenyl)methane-phosphonate dihydrochloride {abbreviated $NH_2$—CH(Am-$C_6H_4$)PO(OPh)$_2$ or (4-AmPhGly)$^P$(OPh)$_2$}

Diphenyl N-benzyloxycarbonylamino(4-amidinophenyl)methanephosphonate hydrochloride {abbreviated Cbz-NH—CH(Am-$C_6H_4$)PO(OPh)$_2$, or Cbz-(4-AmPhGly)$^P$(OPh)$_2$}

Diphenyl N-(N-benzyloxycarbonylprolyl)amino(4-amidinophenyl)methanephosphonate hydrochloride {abbreviated Cbz-NH-Pro-NHCH(Am-$C_6H_4$)PO(OPh)$_2$ or Cbz-Pro-(4-AmPhGly)$^P$(OPh)$_2$}

Diphenyl N-(D-Phe-Pro)arnino(4-amidinophenyl)methanephosphonate dihydrochloride (abbreviated D-Phe-Pro-NHCH(Am-$C_6H_4$)PO(OPh)$_2$ or D-Phe-Pro-(4-AmPhGly)$^P$(OPh)$_2$}

Diphenyl N-(Boc-D-Phe-Pro)amino(4-amidinophenyl) methanephosphonate hydrochloride {abbreviated Boc-D-Phe-Pro-NHCH(Am-C$_6$H$_4$)PO(OPh)$_2$ or Boc-D-Phe-L-Pro-(4-AmPhGly)$^P$(OPh)$_2$}

Diphenyl N-(N-β-napthylsulfonylglycyl)amino(4-amidinophenyl)methanephosphonate hydrochloride {abbreviated naphthylsulfonyl-Gly-NHCH(Am-C$_6$H$_4$) PO(OPh)$_2$ or 2-NpSO$_2$-Gly-(4-AmPhGly)$^P$(OPh)$_2$}

Cbz-(4-AmPhe)$^P$(OPh)$_2$
(4-AmPhe)$^P$(OPh)$_2$·2HCl
Cbz-Pro-(4-CN-Phe)$^P$(OPh)$_2$
Cbz-Pro-(4-AmPhe)$^P$(OEt)$_2$
Boc-D-Phe-Pro-(4-CN-Phe)$^P$(OPh)$_2$
Boc-D-Phe-Pro-(4-AmPhe)$^P$(OPh)$_2$
D-Phe-Pro-(4-AmPhe)$^P$(OPh)$_2$
Boc-Phe-Phe-(4-AmPhGly)$^P$(OPh)$_2$
Cbz-Thr-(4-AmPhGly)$^P$(OPh)$_2$
Boc-Leu-Thr-(4-AmPhGly)$^P$(OPh)$_2$
(4-AmPhGly)$^P$(OPh-4-Cl)$_2$,
Z-(4-AmPhGly)$^P$(OPh4-Cl)$_2$.
Cinnamoyl-(4-AmPhGly)$^P$(OPh)$_2$,
3-(2-Furyl)acryloyl-(4-AmPhGly)$^P$(OPh)$_2$,
3-(3-Thienyl)acryloyl-(4-AmPhGly)$^P$(OPh)$_2$,
3-(2-Pyridyl)acryloyl-(4-AmPhGly)$^P$(OPh)$_2$,
2-Phenoxybenzoyl-(4-AmPhGly)$^P$(OPh)$_2$,
3-Phenoxybenzoyl-(4-AmPhGly)$^P$(OPh)$_2$,
2-Phenoxybenzoyl-Pro-(4-AmPhGly)$^P$(OPh)$_2$,
3-Phenoxybenzoyl-Pro-(4-AmPhGly)$^P$(OPh)$_2$,
2-Phenoxybenzoyl-Pro-Lys$^P$(OPh)$_2$,
3-Phenoxybenzoyl-Pro-Lys$^P$(OPh)$_2$,
2-Phenoxybenzoyl-Pro-HomoLys$^P$(OPh)$_2$, and
3-Phenoxybenzoyl-Pro-HomoLys$^P$(OPh)$_2$.

It has been found that compounds of the present invention have potent antiprotease activity as shown in Table I, Table II, and Table III by effective inhibition of human granzyme A, rat granzyme A, rat granzyme K, mast cell tryptase, bovine trypsin, human thrombin, factor Xa, plasmin, and urokinase. It has been found that compounds of the present invention have anticoagulant activity as shown in Table II and Table III by effective inhibition of the proteolytic function of blood coagulation enzymes in Hepes buffer. It has also been found that compounds of the present invention have anti-tumor activity as shown in Table III by effective inhibition of the proteolytic function of trypsin-like enzymes plasmin and urokinase.

Inactivation rates of serine proteases by aryl diesters of peptidyl derivatives of α-aminoalkylphosphonates were measured by the incubation method. An aliquot of inhibitor (25 or 50 μl) in Me$_2$SO was added to a buffered enzyme solution (0.01–2.3 μM) to initiate the inactivation. Aliquots (50 μl) were withdrawn at various intervals and the residual enzymatic activity was measured. Me$_2$SO concentration in the reaction mixture was 8–12% (v/v). A 0.1 M HEPES, 0.01 M CaCl$_2$, pH 7.5 buffer was utilized for trypsin and trypsin-like enzymes. A 0.1 M HEPES, 0.5 M NaCl, pH 7.5, was utilized for the other serine proteases. The inhibitor concentrations are shown in the Tables I, II, and III. Peptide thioesters or peptide nitroanilides with the appropriate sequences were used as substrates for various serine proteases. All peptide thioesters hydrolysis rates were measured with the assay mixture containing 4,4'-dithiodipyridine {$\epsilon_{324}$=19800 M$^{-1}$cm$^{-1}$; Grasetti & Murray, Arch. Biochem. Biophys. 1967, 119, 41–48}. Peptide 4-nitroanilide hydrolysis was measured at 410 nm {$\epsilon_{410}$=8800 M$^{-1}$cm$^{-1}$; Erlanger et al., Arch. Biochem. Biophys. 1961, 95, 271–278}. First order inactivation rate constants (K$_{obs}$) were obtained from plots of ln v$_t$/v$_o$ vs time, and the correlation coefficients were greater then 0.98.

Anticoagulants can prolong the clotting time of human plasma and play important roles in the treatment of blood coagulation related diseases such as vascular clotting, cerebral infarction and coronary infarction (Williams et al., Hematology, 3rd ed. McGraw Hill, 1983 and Ingram et al., Bleeding Disorders, 2nd ed. Blackwell Scientific Publications, 1985). These two books are incorporated herein by reference. The presence of certain inhibitors of this invention in the human plasma would prolong the prothrombin time, thus these inhibitors would act as anticoagulant in vivo. Currently, there are a few anticoagulant drugs in use clinically, and the inhibitors described in this invention can be used as anticoagulants in the treatment of animals.

The activity of some proteases correlate directly with the invasiveness of tumor cells {Nakajima, M. et al., Science, 1983, 220, 611–613; Sloane, B. F. et al., Cancer Res. 1982, 42, 980–987 and these two articles are incorporated herein by reference}. The tumor invasion can be stopped by treatment with inhibitors of serine proteases {Tryggvason, K. et al., Biochem. Biophys. Acta, 1987, 907, 191–217, and this article is incorporated herein by reference}. Thus the novel inhibitors showed in Table I, Table II, and Table III will be useful for treatment of tumors.

For treatment of blood coagulation-related diseases, tumor invasion or inflammation, the compounds of the present invention may be administered orally, topically or parenterally. The term parenteral as used includes subcutaneous injection, intravenous, intramuscular, intrasternal injection or infusion techniques. The pharmaceutical compositions containing the active ingredient may be in the form suitable for oral use, for example as tablets, troches, lozenges, aqueous or oily suspension, dispersible powders or granules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

To use the above inhibitors in vitro, they are dissolved in an organic solvent such as dimethylsulfoxide or ethanol, and are added to an aqueous solution containing serine proteases. The final concentration of organic solvent should be less than 25%. The inhibitors may also be added as solids or in suspension. The serine protease inhibitors of this invention would be useful in a variety of experimental procedures where proteolysis is a significant problem. Inclusion of these inhibitors in radioimmunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast, and cell lines. The purified cloned product would be obtained in higher yield.

The following examples are given to illustrate the invention and are not intended to limit it in any manner.

General Synthesis Procedures

Benzyl carbamate, triphenyl phosphite, 4-cyanobenzaldehyde, 1,1'-carbonyldiimidazole (CDI), 1,3-dicyclohexylcarbodiimide (DCC), and all common chemicals were obtained from the Aldrich Co., Milwaukee, Wis. Blocked amino acid derivatives were obtained from Aldrich or Bachem Bioscience Inc., Philadelphia, Pa. The NMR spectra were recorded on a Varian Gemini 300 MHz instrument. $^{31}$P NMR spectra were obtained at 161.895 MHz using broad band $^1$H decoupling on a Varian XL-400 instrument; chemical shifts were reported relative to 85% phosphoric acid (sealed capillary) at 0.000 ppm with positive values downfield. Elemental analyses were performed by Atlantic Microlabs of Atlanta, Ga.

EXAMPLE 1

Diphenyl N-benzyloxycarbonylamino(4-cyanophenyl) methanephosphonate {Cbz-(4-CN-PhGly)$^P$(OPh)$_2$} was obtained from 9.75 g of 4-cyanobenzaldehyde, 7.65 g of benzyl carbamate and 13.5 ml of triphenyl phosphite in 20 ml of glacial acetic acid, according to the synthetic procedure described earlier (Oleksyszyn J., Subotkowska L., Mastalerz P., Synthesis, 1979, 985). Yield 70%; mp. 135–138° C.; Anal. Calcd. for C$_{28}$H$_{23}$O$_5$N$_2$P.½H$_2$O: C, 66.27;H, 4.73; N, 5.52. Found: C, 66.03; H, 4.51; N, 5.49.

Cbz-NHCH(4-NO$_2$—C$_6$H$_4$)PO(OPh)$_2$ and Cbz-NHCH (3-Me-C$_6$H$_4$)PO(OPh)$_2$ with m. p. of 151–153° C. and 127–129° C. respectively were obtained by the same procedure using the corresponding benzaldehyde.

Diphenyl N-benzyloxycarbonylamino(4-amidinophenyl)-methanephosphonate hydrochloride {Cbz-(4-AmPhGly)$^P$ (OPh)$_2$}. A solution of 7 g diphenyl N-benzyloxycarbonylamino(4-cyanophenyl)-methanephosphonate in 150 ml of dry chloroform and 15 ml of absolute ethanol was saturated with dry HCl at 0° C. The mixture was kept in the refrigerator until TLC (thin layer chromatography) showed the absence of starting material (about 24 hrs). An excess of pentane was added and the precipitated solid was removed by filtration and dried using a vacuum line. The solid was dissolved in 200 ml of dry methanol and gaseous dry ammonia was passed through the solution (one equivalentsolution (one equivalent is required) for about 20 removed quickly on a rotary evaporator. A 100 ml portion of fresh methanol was added and solution was heated at 50° C. for about 8 hrs until the TLC shows the absence of imino ether. The solvent was evaporated and the resulting oil was dissolved in chloroform. Addition of ether caused the oil to solidify. After filtration the resulting solid was again dissolved in chloroform, the solution was filtered and the solid was precipitated by addition of ether. In several experiments, the yields were 70–80%; mp. 154–158° C. (decomp); $^{31}$P NMR 14.87 ppm. Anal. Calcd. for C$_{28}$H$_{27}$O$_5$N$_3$ClP.0.3 NH$_4$Cl.H$_2$O: C, 57.41; H, 5.16; N, 7.52; Cl, 7.31. Found: C, 57.75; H, 5.00; N, 8.86; Cl, 7.43

An improved amidination procedure was also developed subsequently and should be used in future syntheses. The imino ester is dissolved in a freshly prepared solution of ammonia (1.5 eq.) in methanol, ammonium chloride (1 eq.) is added, and the mixture is then stirred at r.t. for 1 day.

EXAMPLE 2

Diphenyl amino(4-amidinophenyl)methanephosphonate dihydrochloride {(4-AmPhGly)$^P$(OPh)$_2$}. A sample of 1.8 g of diphenyl N-benzyloxycarbonylamino(4-amidinophenyl) methanephosphonate hydrochloride was dissolved in 150 ml of 2N HCl methanol solution and after addition of 5% Pd/C catalyst, the solution was stirred under an atmosphere of hydrogen until the theoretical amount of hydrogen was consumed. The catalyst was removed by filtration and after evaporation of the methanol, the residue was crystallized from ethanol-ether. In several experiments, the yields were 60–80%; mp. 213–215° C.; Anal. Calcd. for C$_{20}$H$_{22}$N$_3$ClP.½H$_2$O: C,51.85; H, 4.97; N, 9.08; Cl, 15.34. Found: C, 51.73; H, 5.02; N, 9.10; Cl, 15.36.

Ala$^P$(4-F-C$_6$H$_4$O)$_2$.HCl, Val$^P$(4-Me-C$_6$H$_4$O)$_2$.HCl, Phe$^P$ (4-Cl-C$_6$H$_4$O)$_2$.HCl can be prepared by the same procedure.

In general, NH$_2$—CH(R)—P(O)(OZ)(OZ$^1$) hydrochloride can be prepared from Cbz—NH—CH(R)—P(O)(OZ) (OZ$^1$) using the same procedure. This intermediate can then be used to prepare a great variety of derivatives by reaction with acylating agents, carbamylating agents, sulfonylating agents, chloroformates, or by coupling with a variety of peptides and blocked peptides using standing peptide coupling reactions, many of which are illustrated in the following examples.

Diphenyl N-(N-benzyloxycarbonylprolyl)amino(4-amidinophenyl)methanephosphonate hydrochloride (Cbz-Pro-(4-AmPhGly)$^P$(OPh)$_2$}. To 0.5 g (2 mmol) of N-benzyloxycarbonylproline in 3 ml of dry DMF at 0° C., 0.45 g (2.77 mmol) of CDI was added and the reaction mixture was stirred at 0° C. for 1 hr. Then 0.9 g (2 mmol) of diphenyl amino(4-amidinophenyl)methanephosphonate hydrochloride was added. After stirring by 18 hrs at 0–5° C., 10 ml of water was added. The oil which precipitated was washed with water and solidified by washing with a cold 0.1 N solution of HCl. One gram of compound was obtained which was used without purification in the next step. $^{31}$P NMR 12.31, 12.62 (free base) and 15.11, 15.41 ppm (hydrochloride). After addition of one drop concentrated HCl to the NMR tube, 14.22, 14.54 ppm (ratio 1:1).

Benzoyl-Ala-Val$^P$(OPh)$_2$, Formyl-Ala-Val$^P$(OPh)$_2$, Fmoc-Ala-Val$^P$(OPh)2 {Fmoc, 9-fluorenylmethyloxycarbonyl}, PhNHCO-Ala-Val$^P$(OPh)$_2$, PhNHCS-Ala-Val$^P$(OPh)$_2$, Dansyl-Ala-Val$^P$(OPh)$_2$, Tosyl-Ala-Val$^P$(OPh)$_2$, Trityl-Ala-Val$^P$(OPh)$_2$, Phthaloyl-Ala-Val$^P$(OPh)$_2$, Cbz-Pro-Ala$^P$(4-F-C$_6$H$_4$O)$_2$, Cbz-Pro-Val$_P$(4-Me-C$_6$H$_4$O)$_2$, Cbz-Pro-Val$^P$(3-Cl-C$_6$H$_4$O)$_2$, Cbz-Pro-Phe$^P$(4-Cl-C$_6$H$_4$O)$_2$, Cbz-Pro-Phe$^P$(4-F-C$_6$H$_4$O)$_2$, Cbz-Ala-Val$^P$(3-Me-C$_6$H$_4$O)$_2$, Cbz-Ala-Phe$^P$(3,4-dichloro-C$_6$H$_3$O)$_2$ can be prepared by the same procedure by coupling with the appropriate blocked amino acid or amino acid derivative.

EXAMPLE 3

Diphenyl N-(D-Phe-Pro)amino(4-amidinophenyl)-methanephosphonate dihydrochloride. One gram of derivative obtained in the previous experiment was hydrogenated in 1 N solution of HCl in methanol with 0.1 g 5% Pd/C, until the theoretical amount of hydrogen was consumed. After filtration of the catalyst and evaporation of the solvent, the resulting oil was dried using a vacuum line. A 0.9 g (1.64 mmol) sample of the product dihydrochloride was added to a solution of 0.43 g (1.64 mmol) of Boc-D-Phe and 0.34 g (2 mmol) of DCI in 2 ml dry DMF, which was allowed to react for 1 hrs at 0° C. After 24 hrs 10 ml of water was added and the oil which precipitated was decanted. After washing with 0.1 N HCl, the oil which solidified was separated by filtration and dried using a vacuum line. The dry solid was dissolved in 1 N HCl solution in methanol and solution was stirred by 1 hr. Solvent was removed on a rotary evaporator and the oil was dried using a vacuum line by several hours to give 0.3 g of product. Yield 24%; mp. 220–224° C.; $^{31}$P NMR, 16.95, 17.25, 17,60 ppm (stereoisomers and conformers). Anal. Calcd. for C$_{34}$H$_{38}$O$_5$N$_2$ClP.5H$_2$O: C, 51.78; H, 6.09; N, 8.88; Cl, 9.00; Found; C, 51.21; H, 5.95; N, 9.04; Cl, 8.97.

EXAMPLE 4

Diphenyl N-(Boc-D-Phe-Pro)amino(4-amidinophenyl)-methanephosphonate hydrochloride {Boc-D-Phe-L-Pro-(4-

AmPhGly)$^P$(OPh)$_2$}. Boc-D-Phe-OH (2.66 g, 10 mmole) and L-Pro-OBzl (2.42 g) were coupled using DCC, and Boc-D-Phe-Pro-OBzl was obtained in 83% yield; $^1$H NMR (CDCl$_3$) δ 7.34 (s, 5H), 7.23 (m, 5H), 5.4 (d, 1H), 5.15 (q, 2H), 4.65 (m, 1H), 4.35 (m, 1H), 3.5 (m, 1H), 3.1–2.9 (m, 2H), 2.6 (m, 1H), 2.–1.7 (m, 4H), 1.43 (s, 9H).

Hydrogenolysis was performed in methanol with 5% water using 5% Pd/C as a catalyst. The product Boc-D-Phe-Pro-OH was obtained as a white solid and recrystallized from aqueous methanol, yield 85%, mp 173–174° C.; $^1$H NMR (DMSO) δ 7.3–7.15 (m, 5H), 7.0 (d, 1H), 4.45(m, 1H), 4.10 (m, 1H), 3.6–2.7 (m, 4H), 2.2–1.6 (m, 4H), 1.30 (s, 9H); MS (FAB$^+$) m/e 363 (M+1); {α}$^{20}{}_D$=−91.5° (0.14 g/mL in methanol). Anal. (C$_{19}$H$_{26}$N$_2$O$_5$) C, H, N.

To 0.36 g (1.0 mmol) of Boc-D-Phe-Pro-OH in 2 ml of dry DMF at 0° C., 0.17 g (1.05 mmol) of CDI was added. After stirring for 1 hr at 0° C., 0.45 g (1.0 mmol) of dihydrochloride of diphenyl amino(4-amidinophenyl)methanephosphonate was added and the solution was stirred for 48 hrs at 0° C. Water (10 ml) was added and the oil which precipitated out was decanted and washed with distilled water. The oil was dissolved in chloroform and the solution was washed with 4% NaHCO$_3$, water, and 0.05 N HCl. After drying over MgSO$_4$, the solvent was removed and the resulting oil was dried on a vacuum line for a few hours to give 0.22 g of product. Yield 29%; mp. 185–190° C.; $^{31}$P NMR, 12.42, 12.66, 12.79 ppm (stereoisomers and conformers) (free base); 15.12, 15.38, 15.58 (hydrochloride). Anal. Calcd. for C$_{39}$H$_{45}$O$_7$N$_5$ClP.1/2H$_2$O: C, 60.75; H, 5.97; N, 9.08; Cl, 4.60. Found: C, 60.98; H, 6.48; N, 8.26; Cl., 4.26.

Tosyl-D-Phe-Pro-Arg$^P$(OPh)$_2$, Cbz-D-Phe-Pro-Arg$^P$(OPh)$_2$, Boc-D-Phe-Pro-Arg$^P$(OPh)$_2$, Boc-D-Phe-Pro-Om$^P$(OPh)$_2$, Boc-D-Phe-Pro-Arg$^P$(4-F-C$_6$H$_4$O)$_2$, Boc-D-Phe-Pro-Arg$_P$(4-Me-C$_6$H$_4$O)$_2$, Boc-D-Phe-Pro-Arg$^P$(3,4-dichloro-C$_6$H$_3$O)$_2$, Boc-D-Phe-Pro-Arg$^P$(3-Cl-C$_6$H$_4$O)$_2$ can be prepared by the same procedure by coupling with the appropriate blocked peptide or peptide derivative.

EXAMPLE 5

Diphenyl N-(N-β-naphylsulfonylglycyl)amino(4-amidino-phenyl)methanephosphonate hydrochloride {2-NpSO$_2$-Gly-(4-AmPhGly)$^P$(OPh)$_2$}. Using the same procedure as example 5, 0.3 g (1.13 mmol) of β-naphylsulfonylglycine, 0.2 g (1.23 mmol) of CDI and 0.45 g (1.0 mmol) of diphenyl amino(4-amidinophenyl)methanephosphonate dihydrochloride (obtained in Example 3) were reacted and 0.21 g of product was obtained. Yield 30%; mp. 205–210° C. (decomp); $^{31}$P NMR, 11.76 ppm (free base), 14.74 ppm (hydrochloride). Anal. Calcd. for C$_{32}$H$_{30}$O$_6$N$_4$ClPS.H$_2$O: C, 56.24; H, 4.69; N, 8.20; S, 4.69. Found: C, 56.87; H, 4.43; N, 8.79; S, 5.06.

EXAMPLE 6

Benzoyl-NHCH(4-NH$_2$—C$_6$H$_4$)PO(OPh)$_2$. NH$_2$CH(4-NO$_2$—C$_6$H$_4$)PO(OPh)$_2$.HBr was obtained by deblocking Cbz-NHCH(4-NO$_2$—C$_6$H$_4$)PO(OPh)$_2$ with 30% of HBr/HOAc, mp. 198–200° C. The reaction of NH$_2$CH(4-NO$_2$—C$_6$H$_4$)PO(OPh)$_2$.HBr and benzoyl chloride in the presence of N-methylmorpholine gave benzoyl-NHCH(4-NO$_2$—C$_6$H$_4$)PO(OPh)$_2$, mp. 157–159° C., mass spectrum m/e=489 (M$^+$+1). Anal. Calc. for C$_{26}$H$_{21}$N$_2$O$_6$P: C, 63.88; H, 4.30; N, 5.73. Found: C, 64.05; H, 4.25; N, 5.69. Hydrogenolysis of benzoyl-NHCH(4-NO$_2$—C$_6$H$_4$)PO(OPh)$_2$ in the presence of Pd/C catalyst gave the final product, mp. 156–158° C., mass spectrum m/e=458 (M$^+$). Anal. Calc. for C$_{26}$H$_{23}$N$_2$O$_4$P: C, 68.12; H, 5.02; N, 6.11. Found: C, 66.87; H, 5.15; N, 5.01.

EXAMPLE 7

4-Cyanophenylacetaldehyde. This compound was prepared from 4-cyanobenzaldehyde using a modification of a procedure previously used in the multi-step synthesis of 2-phenylpropanal {Allen, C. F. H.; van Allan, J., Org. Syn. Coll. Vol 3, 733–734 (1955)}.

Ethyl 3-(4-cyanophenyl)-2,3-epoxypropionate. Ethyl chloroacetate (6.2 g, 50 mmole) and 4-cyanobenzaldehyde (6.6 g, 50 mmole) were dissolved in 100 mL dry benzene. Freshly prepared sodium ethoxide solution in absolute ethanol (1.3 g sodium in 25 mL ethanol) was added and the mixture was stirred at r.t. for 20 h. Water (100 mL) was added with stirring and after several minutes the organic layer was separated, washed with water, dried (MgSO$_4$), filtered, and evaporated to give the desired epoxy product as a yellow oil, yield 70–80%; $^1$H NMR (CDCl$_3$) δ 7.68 (d, 2H), 7.43 (d, 2H), 4.30 (m, 2H), 4.16 (d, 1H), 3.48, (d, 1H), 1.34 (t, 3H).

Sodium 3-(4-cyanophenyl)-2,3-epoxypropionate. Ethyl 3-(4-cyanophenyl)-2,3-epoxypropionate (10.9 g, 50 mmole) was dissolved in 50 mL absolute ethanol and cooled with an ice bath. A freshly prepared sodium ethoxide solution (1.2 g sodium in 25 mL ethanol) was added dropwise during a 10 min period. Dropwise addition of 1 g of water to the stirred mixture caused separation of the sodium salt of the epoxy compound. The mixture was stirred for 3 h, the salt was collected by filtration, washed with 50 mL ethanol and ether several times, and dried, yield 75–85%; $^1$H NMR (D$_2$O) δ 7.58 (d, 2H), 7.33 (d, 2H), 3.93 (d, 1H), 3.39 (d, 1H).

A 1N HCl solution (50 mL, 50 mmole) was added to the sodium salt of the epoxy compound (10.6 g, 50 mmole) dissolved in 50 mL water. This resulted in the separation of an oil which solidifed after a short time. This material was refluxed with 100 mL toluene for 2.5 h to affect decarboxylation. The organic layer was separated, washed with water, dried (Na$_2$SO$_4$), filtered, and evaporated to give 4-cyanophenylacetaldehyde as a yellow brownish oil which solidified after several hours, yield 35–45%. This product is unstable and was used immediately for next step, otherwise polymerization occurs. A sample of the crude product was purified by recrystallization from ether-hexane to give white crystals, mp 63–65° C.; NMR (CDCl$_3$) δ 9.81 (s, 1H), 7.65, (d, 2H), 7.35 (d, 2H), 3.84 (s, 2H); MS m/e 146 (M+1). Anal. (C$_9$H$_7$NO.0.5H$_2$O) C, H, N.

Diphenyl 1-(N-Benzyloxycarbonylamino)-2-(4-cyanophenyl)ethanephosphonate {Cbz-(4-CN-Phe)$^P$(OPh)$_2$}. This compound was synthesized from crude 4-cyanophenylacetaldehyde, benzyl carbamate, and triphenylphosphite using a modification of the previously described amidoalkylation procedure.[9] Benzyl carbamate (6.1 g, 40 mmole) and 4-cyanophenylacetaldehyde (4.7 g, 32 mmole) were dissolved in 50 mL toluene and refluxed for 1 h. The toluene was evaporated, glacial acetic acid (10 mL) and triphenyl phosphite (8.5 mL, 32 mmole) were added to the residue, and the mixture was heated at 80° C. for 2 h. The volatile materials were removed by evaporation in vacuo and the resulting oil was dissolved in 50 mL methanol. The solution was refrigerated overnight and the white precipitate was filtered, dried, and recrystallized from 50 mL hot methanol. The undissolved product was discarded, and the filtrate was cooled down to give white crystals, yield 25–35%; mp 136–137° C.; $^1$H NMR (DMSO) δ 8.20 (d, 1H), 7.75 (d, 2H), 7.54 (d, 2H), 7.35 (m, 5H), 7.3–7.1 (m, 10H), 4.95 (q, 2H), 4.60 (m, 1H), 3.4–3.0 (m, 2H); MS (FAB$^+$) m/e 513 (M+1). Anal. (C$_{29}$H$_{25}$N$_2$O$_5$P) C, H, N.

Diphenyl 1-Amino-2-(4-cyanophenyl)ethanephosphonate Hydrobromide {4-CN-Phe$^P$(OPh)$_2$.HBr}. Cbz-(4-CNPhe)$^P$(OPh)$_2$ (0.57 g, 1.1 mmole) was mixed with 1.0 mL 30% HBr in acetic acid. The mixture was protected against moisture and kept at r.t. for 1 h. Addition of 50 mL dry ether and stirring for several hours resulted in formation of a yellow brownish solid which was filtered, washed with ether, and dried to give the product (0.48 g, 95%); mp 197–199° C.; $^1$H NMR (DMSO) δ 9.0 (b, 3H), 7.85 (d, 2H), 7.65 (d, 2H), 7.4–7.0 (m, 10H), 4.7 (m, $^1$H), 3.4 (m, 2H); MS (FAB$^+$) m/e 379 (M—Br).

Diphenyl 1-(N-Benzyloxycarbonylamino)-2-(4-amidinophenyl)ethanephosphonate {Cbz-(4-AmPhe)$^P$(OPh)$_2$}. Cbz-(4-CNPhe)$^P$(OPh)$_2$ (1.03 g, 2.0 mmole) was dissolved in a mixture of methanol and chloroform (1:1, 20 mL). The solution was cooled to 0° C., saturated with dry HCl, the solution was kept at 5° C. for 48 h, and then the solvent was evaporated at r.t. in vacuo. The resulting semisolid was treated with 50 mL dry ether, filtered, washed with dry ether, and dissolved in 10 mL methanol containing 51 mg (3.0 mmole) ammonia. Ammonium chloride (107 mg, 2.0 mmole) was added, the mixture was stirred at r.t. for 1 day, the solvent was removed at r.t. in vacuo and the resulting semisolid was dissolved in 50 mL chloroform, filtered, and the filtrate was evaporated to give the crude product. The crude product was treated with 50 mL dry ether, stirred, and the undissolved solid collected, washed with ether and dried to give the amidine product as a yellow powder, yield 50–70%; mp >140 (dec); $^1$H NMR (DMSO) δ 9.4–9.2 (d, 4H), 8.25 (d, 1H), 7.8 (d, 2H), 7.6 (d, 2H), 7.38 (m, 5H), 7.3–7.1 (m, 10H), 4.95 (q, 2H), 4.6 (m, 1H), 3.4–3.1 (m, 2H); MS (FAB$^+$) m/e 530 M—Cl). Anal. (C$_{29}$H$_{29}$N$_3$O$_5$ClP) C, H, N.

EXAMPLE 8

Diphenyl 1-Amino-2-(4-amidinophenyl) ethanephosphonate {(4-AmPhe)$^P$(OPh)$_2$.2HCl}. The amidine Cbz-(4-AmPhe)$^P$(OPh)$_2$ (1.0 g, 1.76 mmole) was dissolved in 150 mL methanol containing 2 mmole HCl, a catalyst (0.5 g of 5% Pd/C) was added, and the mixture was hydrogenated. After hydrogenolysis, the catalyst was removed by filtration and the filtrate was evaporated to give a near white crystalline product, yield 85–90%; mp >180 (dec.); $^1$H NMR (DMSO) δ 9.5–9.3 (d, 4H), 9.2–9.0 (m, 3H), 7.9–7.1 (m, 14H), 4.55 (m, 1H), 3.2–3.5 (m, 2H); MS (FAB$^+$) m/e 396 (M+1−2HCl). Anal. (C$_{21}$H$_{24}$N$_3$O$_3$Cl$_2$P) C, H, N.

EXAMPLE 9

Diphenyl 1-(N-Benzyloxycarbonyl-L-prolyl)amino-2-(4-cyanophenyl)ethanephosphonate {Cbz-Pro-(4-CN-Phe)$^P$(OPh)$_2$}. To a cooled solution of the phosphonate 4-CN-Phe$^P$(OPh)$_2$.HBr (0.41 g, 0.9 mmole) and Cbz-Pro-OH (0.25 g, 1.0 mmole) in 20 mL CH$_2$Cl$_2$ was added 0.14 mL triethyl amine. After stirring for 10 min, DCC (0.21 g, 1.0 mmole) was added and the mixture was stirred at 0° C. for 2 h and at r.t. for 24 h. During this period, dicyclohexylurea (DCU) formed, was removed by filtration and the filtrate was evaporated. The residue was dissolved in 50 mL ethyl acetate, filtered, the filtrate was washed with 50 mL 1N HCl, water, 6% NaHCO$_3$, and water. The organic layer was dried, filtered, and evaporated to give crude product which was then recrystallized from ether to give white crystals, yield 52% (0.29 g); mp 131–132° C.; $^1$H NMR (DMSO) δ 8.75(m, 1H), 7.8–7.2(m, 19H), 5.06 (m, 2H), 4.95 (m, 1H), 4.6 (q, 1H), 4.2 (m, 1H), 3.5–3.1 (m, 3H), 2.0–1.4 (m, 4H); MS (FAB$^+$) m/e 610 (M+1). Anal. (C$_{34}$H$_{32}$N$_3$O$_6$P) C, H, N.

EXAMPLE 10

Diethyl 1-(N-benzyloxycarbonyl-L-prolyl)amino-2-(4-amidinophenyl)ethanephosphonate {Cbz-Pro-(4-AmPhe)$^P$(OEt)$_2$, 10}. This compound was obtained during the amidination procedure of dipeptide Cbz-Pro-(4-CN-Phe)$^P$(OPh)$_2$ when ethanol was used instead of methanol. Transesterification occurred and the phenyl groups were replaced by ethyl groups, yield 50% (0.11 g); mp >130° C. (dec); $^1$H NMR (DMSO) δ 9.4–9.2 (m, 4H), 8.4 (m, 1H), 7.8–7.1 (m, 9H), 5.0 (s, 2H), 4.5 (m, 1H), 4.2 (m, 1H), 4.0 (m, 4H), 3.5–2.9 (m, 4H), 2.1–1.4 (m, 4H), 1.25 (m, 6H); MS (FAB$^+$) m/e 531 M—Cl). Anal. (C$_{26}$H$_{36}$N$_4$O$_6$ClP) C, H, N.

EXAMPLE 11

Diphenyl 1-(N-t-Butyloxycarbonyl-D-phenylalanyl-L-prolyl)amino-2-(4-cyanophenyl)ethanephosphonate {Boc-D-Phe-Pro-(4-CN-Phe)$^P$(OPh)$_2$}. The phosphonate 4-CN-Phe$^P$(OPh)$_2$.HBr (0.46 g, 1 mmole) was coupled with Boc-D-Phe-Pro-OH (0.36 g, 1.0 mmole) using DCC. The product was obtained as a glass-like solid, yield 86% (0.62 g); mp 85–90° C.; $^1$H NMR (DMSO) δ 8.25 (2d, 1H), 7.8–7.0 (m, 19H), 4.8 (m, 1H), 4.4 (m, 1H), 4.3 (m, 1H), 4.2 (m, 1H), 3.5–2.8 (m, 4H), 2.0–1.4 (m, 4H), 1.3 (m, 9H); MS (FAB$^+$) m/e 723 (M+1). Anal. (C$_{40}$H$_{43}$N$_4$O$_7$P.0.25 H$_2$O) C, H, N.

EXAMPLE 12

Diphenyl 1-{(N-t-Butyloxycarbonyl-D-phenylalanyl-L-prolyl)amino}-2-(4-amidinophenyl)ethanephosphonate {Boc-D-Phe-Pro-(4-AmPhe)$^P$(OPh)$_2$}. CDI (0.13 g, 0.8 mmole) was added to Boc-D-Phe-Pro-OH (0.24 g, 0.67 mmole) in 2 mL DMF. A solution of amidine (4-AmPhe)$^P$(OPh)$_{2.2}$HCl (0.31 g, 0.67 mmole) in 2 mL DMF was added to a cooled solution (0° C.) of the peptide and the mixture was incubated at 0° C. for 2 h and r.t. for 48 h. DMF was removed in vacuo and the residue oil was dissolved in 100 mL CHCl$_3$, filtered, and the organic layer was washed subsequently with 50 mL 0.05 M HCl, 10% KCl, 6% NaHCO$_3$, and water. The organic layer was dried, filtered, and evaporated to give a crystalline product which was then dried in vacuo, yield 59% (0.31 g); mp 145–155° C. (dec.); $^1$H NMR (DMSO) δ 10.1–9.7 (m, 2H), 9.4–9.0 (m, 3H), 8.0–7.0 (m, 19H), 6.75 (m, 1H), 4.9–4.0 (m, 3H), 3.5–2.6 (m, 6H), 2.0–1.4 (m, 4H), 1.3 (s, 9H); MS (FAB$^+$) m/e 740 M—Cl). Anal. (C$_{40}$H$_{46}$N$_5$O$_7$P.0.3HCl.1.5H$_2$O) C, H, N.

EXAMPLE 13

Diphenyl 1-(N-(D-Phenylalanyl-L-prolyl)amino-2-(4-amidinophenyl)ethanephosphonate Dihydrochloride {D-Phe-Pro-(4-AmPhe)$^P$(OPh)$_2$}. Boc-D-Phe-Pro-(4-AmPhe)$^P$(OPh)$_2$ (0.11 g) was dissolved in 2 mL CHCl$_3$ and the solution was saturated with dry HCl. An oily precipitate formed and the mixture was kept at r.t. for 2 h before evaporating to dryness to obtain the crystalline product, yield 80% (0.08 g); mp >165° C. (dec); $^1$H NMR (DMSO) δ 9.4–9.2 (d, 4H), 8.5 (m, 3H), 8.2 (m, 1H), 7.9–7.0(m, 19H), 4.8–3.9 (m, 3H), 3.5–2.8 (m, 6H), 2.0–1.1 (m, 4H); MS (FAB$^+$) m/e 640 (M+1−2Cl). Exact mass calcd. for C$_{35}$H$_{39}$N$_5$O$_5$P (M+1−2HCl) 640.2689. Found: 640.2786.

EXAMPLE 14

Boc-Phe-Phe-(4-AmPhGly)$^P$(OPh)$_2$. To a THF solution (5 ml) of Boc-Phe-Phe-OH (0.21 g, 0.5 mmol) was added successively N-methylmorpholine (55 μl, 0.5 mmol) and isobutyl chloroformate (65 μl, 0.5 mmol) at −15° C. After stirring for 2 min and addition of cold THF solution (1 ml) of triethylamine (70 μl, 0.5 mmol), the mixture was added to a DMF solution (1 ml) of (4-AmPhGly)$^P$(OPh)$_2$. 2HCl (0.23 g, 0.5 mmol) at −15° C. After stirring at −15° C. for 1 hr and at 0–5° C. for 12 hr, the reaction mixture was concentrated in vacuo. The residue was triturated with ether and was purified by chromatography (silica gel, CHCl$_3$/CH$_3$OH, 14:1) and solidified from ether to give the final product (80 mg, 20% yield) as a white powder; mp 149–170° C., R$_f$=0.45 (CHCl$_3$/CH$_3$OH/CH$_3$CO$_2$H, 80:10:5), Anal. Calcd. for C$_{43}$H$_{47}$O$_7$N$_5$Cl.H$_2$O: C, 62.2; H, 5.95; N, 8.43. Found: C, 62.3; H, 6.01; N, 8.45.

EXAMPLE 15

5-Phthalimidopentanol. A mixture of phthalic anhydride (6.46 g, 43.6 mmol) and 5-aminopentanol (4.5 g, 43.6 mmol) was heated to 145° C. in an open flask for 30 min. A stream of N$_2$ was applied to expel water vapor. After cooled to room temperature, the reaction residue was dried on vacuum pump. The product was obtained as colorless oil: yield 100%; $^1$H NMR (CDCl$_3$) δ 1.4–1.5 (m, 2H), 1.6–1.8 (m, 4H), 3.6 (t, 2H, J=6.5), 3.7 (t, J=7.2 Hz), 7.7 (m, 2H), 7.8–7.9 (m, 2H).

5-Phthalimidopentanal. The preparation of this compound begins by adding oxaly chloride (4.6 mL, 53.2 mmol) to 60 mL of freshly distilled CH$_2$Cl$_2$ containing DMSO (6.9 mL, 96.0 mmol) at −45° C., and stirring for 5 min. The dropwise addition (over 20 min) of phthalic alcohol (10.2 g, 43.6 mmol) in 40 mL CH$_2$Cl$_2$ was followed by an additional 15 min stirring, and then DIEA (22.8 mL, 130.9 mmol) was introduced. At this time the reaction temperature was warmed to −30° C. and stirring continued for 30 min. The solvent was removed and the residue was taken-up in 100 mL EtOAc, filtered to remove any DIEA salt, washed with 6% NaHCO$_3$ and water (3×40 mL), and dried over Na$_2$SO$_4$. After filtering the solvent was removed yielding the aldehyde, a yellow oil: yield 88%; $^1$H NMR (CDCl$_3$) δ 1.6–1.9 (m, 4H), 2.5 (t, J=6.3 Hz, 2H), 3.7 (t, J=7.8, 2H), 7.6–7.9 (m, 4H), 9.7 (s, 1H); MS (EI$^+$) m/z 231.1.

Diphenyl N-(N-Benzyloxycarbonyl)amino(4-phthalimidobutyl)methanephosphonate {Cbz-Lys(Pht)$^P$(OPh)$_2$)}. To a mixture of 5-phthalimidopentanal (8.9 g, 38.5 mmol), triphenylphosphite (10.1 mL, 38.5 mmol) and benzyl carbamate (5.8 g, 38.5 mmol) was added 100 mL acetic acid. The solution was stirred at 80–90° C. for one hour. Acetic acid was removed in vacuo. Crystallizing from methanol yielded the phosphonate product as a white solid: mp 100–102° C.; yield 29.1%; $^1$H NMR (CDCl$_3$) δ 1.5–2.2 (m, 6H), 3.7 (t, 2H, J=6.3 Hz,), 4.4–4.6 (m, 1H), 5.0–5.3 (m, 2H), 7.0–7.4 (m, 15H), 7.7 (m, 2H), 7.9 (m, 2H). Anal. (C$_{33}$H$_{31}$O$_7$N$_2$P) C, H, N. The analytical data are consistent with reported data.[32]

Diphenyl N-(N-Benzyloxycarbonyl)amino(4-aminobutyl)methanephosphonate Hydrochloride {Cbz-Lys$^P$(OPh)$_2$}. Cbz-Lys(Pht)$^P$(OPh)$_2$ (0.6 g, 1.0 mmol) was dissolved in hot i-PrOH (60° C.) followed by addition of hydrazine (0.1 mL, 3.0 mmol) via a syringe. The reaction mixture was allowed to stir for three hours at 60° C. The solid formed was filtered and the solvent was removed. The remaining residue was taken up in 100 mL of CHCl$_3$, and washed with saturated NaCl (4×60 mL) and then dried over Na$_2$SO$_4$. After the CHCl$_3$ solution was cooled to 0° C. the solution was saturated with gaseous HCl. Finally, the solvent was removed and the residue was triturated in ether to give the product as white solid: mp 123–126° C.; yield 75%; $^1$H NMR (DMSO) δ 1.4–2.0 (m, 6H), 2.7–2.8 (m, 2H), 4.2–4.4 (m, 1H), 5.0–5.2 (m, 2H), 7.1–7.4 (m, 15H), 7.8–8.1 (m, 3H); MS (FAB$^+$) m/z calcd for C$_{15}$H$_{29}$O$_5$N$_2$P (M+1) 469.3. Anal. (C$_{25}$H$_{29}$O$_5$N$_2$P.HCl.0.7H$_2$O) C, H, N.

EXAMPLE 16

4-Phthalimidobutanol. This compound, a colorless oil, was prepared in the same manner as 5-phthalimidopentanol: yield 100%; $^1$H NMR (CDCl$_3$) δ 1.6–1.7 (m, 2H), 1.7–1.9 (m, 2H), 3.7 (t, J=7.7 Hz, 2H), 4.35 (t, J=6.4 Hz, 1H), 7.7–7.8 (m, 2H), 7.8–7.9 (m, 2H), 7.8–7.9 (m, 2H).

4-Phthalimidobutanal. This compound, a colorless oil, was prepared in the same manner as 5-phthalimidopentanal; yield 38%; $^1$H NMR (CDCl$_3$) δ 2.0–2.1 (m, 2H), 2.5–2.6 (td, J=6.0, 1.1, 2H), 3.7–3.8 (t, J=6.8 Hz, 2H), 7.7–7.8 (m, 2H), 7.8–7.9 (m, 2H), 9.8 (s, 1H); MS (EI$^+$) $^{m/z}$ 217.1.

Diphenyl N-(N-Benzyloxycarbonyl)amino(3-phthalimidopropyl)methanephosphonate {Cbz-Orn(Pht)$^P$(OPh)$_2$}. This compound was prepared in the same manner as Cbz-Lys(Pht)$^P$(OPh)$_2$: mp 72–74° C.; yield 47%; $^1$H NMR (CDCl$_3$) δ 1.5–2.2 (m, 4H), 3.8 (t, J=6.8 Hz, 2H), 4.5–4.7 (m 1H), 5.0–5.2 (m, 2H), 7.0–7.4 (m, 15H), 7.7 (m, 2H), 7.9 (m, 2H); MS (FAB$^+$) m/z 585.0.

Diphenyl N-(N-Benzyloxycarbonyl)amino(3-aminopropyl)methanephosphonate {Cbz-Orn$^P$(OPh)$_2$}. This compound was prepared in the same manner as Cbz-Lys$^P$(OPh)$_2$ with exception that the product was obtained as an acetate salt: 111–113° C.; yield 66%; $^1$H NMR (DMSO) δ 1.8 (s, 3H), 1.5–2.1 (m, 4H), 2.6–2.7 (m, 2H), 4.2–4.4 (m, 1H), 5.0–5.2 (m, 2H), 7.1–7.5 (m, 15H), 8.1 (br s, 1H); MS (FAB$^+$) m/z 455.0. Anal (C$_{24}$H$_{27}$O$_5$N$_2$P.C$_2$H$_4$O$_2$) C, H, N.

EXAMPLE 17

6-Phthalimidohexanol. This compound was prepared in the same manner as 5-phthalimidohexanol from 6-aminohexanol (3.51 g, 30.0 mmol) and phthalic anhydride (4.44 g, 30.0 mmol) to give the product as brown oil: yield 91%; $^1$H NMR (CDCl$_3$) δ 1.3–1.8 (m, 8H), 3.6–3.7 (m, 4H), 4.3 (t, J=6.5 Hz, 1H), 7.7 (m, 2H), 7.8 (m, 2H).

6-Phthalimidohexanal. This compound was prepared in the same manner as 5-phthalimidopentanal from 6-phthalimidohexanol (6.73 g, 27.2 mmol), DMSO (4.3 mL, 59.8 mmol), oxalyl chloride (2.9 mL, 32.7 mmol) and DIEA (14.2 mL, 81.7 mmol) to give the product as light brown oil: yield 81%; 1H NMR (CDCl$_3$) o 1.4 (m, 2H) 1.7 (m, 4H), 2.5 (td, J=7.1, 1.2 Hz, 2H), 3.7 (t, J=6.3 Hz, 2H), 7.7–7.9 (m, 4H), 9.8 (s, 1H).

Diphenyl N-(N-Benzyloxycarbonyl)amino(6-phthalimidohexyl)methanephosphonate {Cbz-HomoLys(Pht)$^P$(OPh)$_2$}. This compound was prepared in same manner as Cbz-Lys(Pht)$^P$(OPh)$_2$ from 6-phthalimidohexanal (5.38 g, 22.0 mmol), triphenylphosphite (5.75 g, 22.0 mmol) and benzyl carbamate (3.33 g, 22.0 mmol) to give the product as a light brown solid: mp 95–96° C.; yield 40%; $^1$H NMR (CDCl$_3$) δ 1.3–2.1 (m, 8H), 3.7 (t, J=6.6 Hz, 2H), 4.4–4.5 (m, 1H), 5.1–5.2 (m, 2H), 7.0–7.4 (m, 15H), 7.7 (m, 2H), 7.9 (m, 2H). Anal (C$_{34}$H$_{33}$O$_7$N$_2$P) C, H, N.

Diphenyl N-(N-Benzyloxycarbonyl)amino(6-aminohexyl)methanephosphonate {Cbz-HomoLys$^P$(OPh)$_2$}. This compound was prepared in same manner as Cbz-Lys$^P$(OPh)$_2$: mp 69–71° C.; yield 59%; $^1$H NMR (CDCl$_3$) δ 1.2–2.0 (m, 8H), 2.7–2.9 (br s, 2H), 4.4 (m, 1H), 5.0 (m, 2H), 6.0 (d, J=9.6 Hz, 1H), 7.0–7.3 (m, 15H), 8.0–8.2 (br s, 3H); MS (FAB$^+$) m/z 483.1.

EXAMPLE 18

Diphenyl N-(trans-Cinnamoyl)amino(4-amidinophenyl) methanephosphonate Hydrochloride {trans-Cinnamoyl-(4-AmPhGly)$^P$(OPh)$_2$}; mp 111–118° C.; yield, 18%; $^1$H NMR (DMSO) δ 5.2–5.4 (m, 1H), 6.1–6.4 (m, 1H), 6.6–6.8 (m, 2H), 6.9–7.65 (m, 16H), 7.65–8.0 (m, 3H), 8.4–8.6 (m, 1H), 8.7–8.9 (m, 1H), 9.1–9.7 (m, 3H); MS (FAB$^+$) m/z 512.2. Anal. (C$_{29}$H$_{26}$O$_4$N$_3$P.HCl.H$_2$O) C, H, N.

EXAMPLE 19

Diphenyl N-(3-(2-Furyl)acryloyl)amino(4-amidinophenyl)methanephosphonate Hydrochloride {3-(2-Furyl)acryloyl-(4-AmPhGly)$^P$(OPh)$_2$, 17}; mp 97–105° C.; yield, 10%; $^1$H NMR (DMSO) δ 6.1–6.3 (dd, $^1$H, J=9.8 Hz), 6.55–6.63 (m, 1H), 6.7–6.8 (m, 2H), 6.83–6.84 (d, 1H, J=3.3 Hz), 7.0–7.1 (m, 4H), 7.1–7.25 (m, 3H), 7.3–7.4 (m, 4H), 7.45–7.65 (m, 1H), 7.8–7.95 (m, 4H), 9.2–9.4 (m, 3H), 9.6–9.65 (m, 1H); MS (FAB$^+$) m/z 502.4. Anal. (C$_{27}$H$_{24}$O$_5$N$_3$P.HCl) C, H, N.

EXAMPLE 20

Diphenyl N-(3-(2-Thienyl)acryloyl)amino(4-amidinophenyl)methanephosphonate Hydrochloride {3-(2-Thienyl)acryloyl-(4-AmPhGly)$^P$(OPh)$_2$, 18}; mp 114–119° C.; yield, 17%; $^1$H NMR (DMSO) δ 6.15–6.25 (dd, $^1$H, J=9.0 Hz), 6.65–6.85 (m, 2H), 7.0–7.15 (m, 5H), 7.15–7.25 (m, 2H), 7.3–7.45 (m, 5H), 7.6–7.71 (m, 2H), 7.8–7.9 (m, 4H), 9.5–9.6 (m, 1H), 9.65–10.1 (br s, 3H); MS (FAB$^+$) m/z 518.0. Anal. (C$_{27}$H$_{24}$O$_4$N$_3$SP.0.5HC.H$_2$O) C, H, N.

EXAMPLE 21

Diphenyl N-(trans-3-(3-Pyridyl)acryloyl)amino(4-amidinophenyl)methanephosphonate Hydrochloride {trans-3-(3-Pyridyl)acryloyl-(4-AmPhGly)$^P$(OPh)$_2$}; mp 103–109° C.; yield, 17%; $^1$H NMR (DMSO) δ 6.15–6.3 (m, 1H), 6.7–6.8 (d, 1H), 6.9–7.6 (m, 14H), 7.7–8.1 (m, 5H), 8.5–8.6 (m, 1H), 8.7–8.9 (m, 1H), 9.1–9.7 (br s, 2H), 9.9–10.0 (m, 1H); HRMS (FAB$^+$) m/z calcd. for C$_{28}$H$_{25}$O$_4$N$_4$P (M+1) 513.1692, found 513.1730. Reversed phase HPLC (90% MeCN-H$_2$O), t$_R$=2.51 min.

EXAMPLE 22

Diphenyl N-(3-Phenoxybenzoyl)amino(4-amidinophenyl)methanephosphonate Hydrochloride {3-Phenoxybenzoyl-(4-AmPhGly)$^P$(OPh)$_2$}; mp 85–93° C.; yield, 32%; $^1$H NMR (DMSO) δ 6.2–6.4 (m, 1H), 7.0–7.3 (m, 10H), 7.3–7.5 (m, 8H), 7.6–7.7 (m, 2H), 7.8–8.0 (m, 4H), 9.2–10 (m, 4H); HRMS (FAB$^+$) m/z (M+Cl) calcd. for C$_{33}$H$_{28}$O$_5$N$_3$P 578.1845, found 578.1828. Anal. (C$_{33}$H$_{28}$O$_5$N$_3$P.HCl.0.75DMF) C, H, N.

EXAMPLE 23

Diphenyl N-(2-Phenoxybenzoyl)amino(4-amidinophenyl)methanephosphonate Hydrochloride {2-Phenoxybenzoyl-(4-A mPhGly)$^P$(OPh)$_2$}; mp 85–93° C.; yield, 28%; $^1$H NMR (DMSO) δ 6.1–6.3 (m, 1H), 6.9–7.1 (m, 5H), 7.1–7.26 (m, 3H), 7.26–7.4 (m, 7H), 7.45–7.6 (m, 3H), 7.75–7.9 (m, 6H), 9.5–10.5 (m, 4H); MS (FAB$^+$) m/z 578.0. Anal. (C$_{33}$H$_{28}$O$_5$N$_3$P.HCl.1.5H$_2$O) C, H, N.

EXAMPLE 24

Diphenyl N-(N-(2-Phenoxybenzoylprolyl))amino(4-amidinophenyl)methanephosphonate Hydrochloride {(2-Phenoxybenzoyl)-Pro-(4-AmPhGly)$^P$(OPh)$_2$}. Mp 90–95° C.; yield, 43%; $^1$H NMR (DMSO) δ 1.55–1.9 (m, 3H), 2.05–2.3(m, 1H), 3.2–3.6 (m, 2H), 4.5–4.7 (m, 1H), 5.8–6.15 (m, 1H), 6.7–7.6 (m, 19H), 7.7–7.9 (m, 4H), 9.15–9.5 (m, 4H); HRMS (FAB$^+$) m/z calcd for C$_{38}$H$_{35}$O$_6$N$_4$P (M+1) 675.2372, found 675.2338. Anal. (C$_{38}$H$_{35}$O$_6$N$_4$P.HCl.0.5DMF) C, H, N.

EXAMPLE 25

Diphenyl N-(N-(3-Phenoxybenzoylprolyl))amino(4-amidinophenyl)methanephosphonate Hydrochloride {(3-Phenoxybenzoyl)-Pro-(4-AmPhGly)$^P$(OPh)$_2$}. Mp 104–110° C.; yield, 33%; 1H NMR (DMSO) δ 1.5–1.9 (m, 3H), 2.1–2.3 (m, 1H), 3.2–3.6 (m, 2H), 4.5–4.8 (m, 1H), 5.9–6.2 (m, 1H), 6.7–6.9 (m, 1H), 6.9–7.3 (m, 11H), 7.3–7.5 (m, 7H), 7.7–7.9 (m, 4H), 9.1–9.4 (m, 1H), 9.4–9.6 (m, 1H), 9.6–10.0 (br s, 2H); MS (FAB$^+$) m/z 675.1. Anal. (C$_{38}$H$_{35}$O$_6$N$_4$P.HCl.1/3H$_2$O) C, H, N.

EXAMPLE 26

Synthesis of Derivatives of Orn$^P$(OPh)$_2$, Lys$^P$(OPh)$_2$ and HomoLys$^P$(OPh)$_2$ (General Procedure C). The general procedures for synthesizing peptidyl phosphonate derivatives of lysine and homolysine follows: the blocked phosphonate Cbz-Lys(Pht)$^P$(OPh)$_2$ (1 mmol) or Cbz-HomoLys(Pht)$^P$(OPh)$_2$ (1 mmol) were dissolved in 20 mL 30% HBr in acetic acid at room temperature. After 30 min, the acetic acid was removed under reduced pressure. The residue was triturated in Et$_2$O to obtain HBr-H-Lys(Pht)$^P$(OPh)$_2$ or HBr.H-HomoLys(Pht)$^P$(OPh)$_2$. A mixture of HBr.H-Lys (Pht)$^P$(OPh)$_2$ (1 mmol) or HBr.H-HomoLys(Pht)$^P$(OPh)$_2$ (1 mmol), HOBt (0.6 mmol) and an amino acid or peptide component (1.2 mmol) were added to 5 mL dry DMF followed by addition of Et$_3$N (1.2 mmol). EDC (1.4 mmol) was then added at 0° C. and the reaction mixture was allowed to stir overnight at 2° C. Any precipitate that formed was removed by filtration followed by evaporation of the solvent under reduced pressure. The residue was redissolved in 60 mL EtOAc and washed with 50 mL 0.6 M HCl, water, and 6% NaHCO$_3$, respectively. The solution was dried over Na$_2$SO$_4$, the solvent removed, and the crude product purified by column chromatography (silica gel, elution with CHCl$_3$,EtOAc=1:1). The purified peptidyl-Lys(Pht)$^P$(OPh)$_2$ (0.3 mmol) or peptidyl-HomoLys(Pht)$^P$(OPh)$_2$ (0.3 mmol) was dissolved in 6 mL of isopropanol followed by addition of anhydrous hydrazine (0.9 mmol). The reaction mixture was stirred overnight at room temperature, a white precipitate was removed by filtration, and the solvent was evaporated. The residue was taken up in 50 mL of CHCl$_3$, the solution was washed with 3×30 mL water and dried over Na$_2$SO$_4$. Gaseous HCl was then bubbled through the chloroform solution for 3 min. The final product was obtained by triturating the residue with ether after removal of the CHCl$_3$. Some of the derivatives of peptidyl-Lys$^P$(OPh)$_2$ or peptidyl-HomoLys$^P$(OPh)$_2$ were found to contain small amount of N$_2$H$_4$.HCl as a byproduct. The NMR spectra shown a small peak at around δ 7.0 which is identical to an authentic sample confirming the existence of the salt. These lysine or homolysine phosphonate derivatives were used without further purification.

All final products were characterized by NMR, mass spectroscopy (MS) or high resolution MS and elemental analysis.

EXAMPLE 27

Diphenyl N-Benzyloxycarbonylamino-(3-amidinophenyl)methanephosphonate Hydrochloride {Cbz- (3-AmPhGly)$^P$(OPh)$_2$}. This compound was synthesized by general procedure A starting with 3-cyanobenzaldehyde. Ethanol was used as solvent instead of methanol when synthesizing the iminoester. The product was obtained as a white solid: mp 87–89° C.; yield, 84%; $^1$H NMR (DMSO-d$_6$) δ 5.0–5.2 (m, 2H), 5.6–5.8 (m, 1H), 7.0–7.4 (m, 16H), 7.7–7.8 (m, 3H), 8.0 (s, 1H), 8.9–9.4 (m, 4H); HRMS (FAB$^+$) m/z calcd. for C$_{28}$H$_{27}$N$_3$O$_5$ClP (M+H)$^+$516.1688, found 516.1688. Anal. (C$_{28}$H$_{26}$N$_3$O$_5$ClP.HCl.H$_2$O) C, H, N.

EXAMPLE 28

Di-p-chlorophenyl N-Benzyloxycarbonylamino-(4-amidinophenyl)methanephosphonate Hydrochloride {Cbz-(4-AmPhGly)$^P$(OPh-p-Cl)$_2$}. This compound was synthesized starting with tri-para-chlorophenylphosphite. DMF was used at the amidination stage to prevent transesterification which occurred when MeOH was used as the solvent. The product was obtained as a white solid: mp 123–130° C.; yield, 66%; $^1$H NMR (DMSO-d$_6$) δ 5.0–5.2 (q, 2H), 5.7–5.9 (m, 1H), 7.0–8.0 (m, 8H), 9.0–9.4 (m, 4H); HRMS (FAB$^+$) m/z calcd. for C$_{28}$H$_{25}$N$_3$O$_5$Cl$_2$P (M+H)$^+$584.0909, found 584.0934. Anal. (C$_{28}$H$_{24}$N$_3$O$_5$ClP.HCl.H$_2$O) C, H, N.

EXAMPLE 29

Methyl Phenyl N-Benzyloxycarbonylamino-(4-amidinophenyl)methanephosphonate Hydrochloride {Cbz-(4-AmPhGly)$^P$(OPh)(OMe)}. Cbz-(4-CNPhGly)$^P$(OPh)$_2$ (1 mmol) was dissolved in 45% MeOH in CHCl$_3$. The solution was saturated with gaseous HCl at 0° C. The reaction mixture was allowed to stir overnight followed by the removal of solvent on a rotary evaporator at 20° C. The residue was triturated in Et$_2$O. The solid obtained was redissolved in 100 mL MeOH. The methanol solution was then saturated with gaseous NH$_3$. The reaction mixture was stirred at 0° C. for one hour and the solvent was evaporated under reduced pressure. Fresh methanol (100 mL) was then added to the residue and the solution was stirred for one day at 50° C. The methanol was then removed followed by the addition of CHCl$_{13}$ (100 mL). Gaseous HCl was bubbled through the solution for 5 min at 0° C. After removal of the CHCl$_3$, the residue was triturated in Et$_2$O. The product was obtained as a white solid and used without further purification: mp 100–106° C.; yield, 46%; $^1$H NMR (DMSO-d$_6$) δ 3.5–3.7 (m, 3H), 5.0–5.2 (m, 2H), 5.5 (m, 1H), 7.0–7 (m, 12H), 7.6–8.0 (m, 4H), 8.8–9.4 (m, 4H); HRMS (FAB$^+$) m/z calcd. for C$_{23}$H$_{24}$O$_5$N$_3$P (M+H)$^+$454.1532, found 454.1515; HPLC (90% CH$_3$CN/H$_2$O and 10% CH$_3$CN/H$_2$O) single peak (>95%) with traces of three byproducts, t$_R$=11.6 min. Anal. (C$_{23}$H$_{24}$N$_3$O$_5$P.HCl.0.5Et$_2$O) C, H, N.

EXAMPLE 30

Phenyl Hydrogen N-Benzyloxycarbonylamino-(4-amidinophenyl)methanephosphonate Hydrochloride {Cbz-(4-AmPhGly)$^P$(OPh)(OH)}. The phosphonate Cbz-(4-AmPhGly)$^P$(OPh)$_2$ (0.55 g, 1.0 mmol) and cis-dicyclohexane 18-crown-6 (0.037 g, 0.1 mmol) were dissolved in 10 mL of a mixture of DMF/water (80%, v/v) followed by addition of a 30% ammonia solution (0.16 mL, 2.6 mmol). The reaction mixture was allowed to stir for 3 days. The reaction was monitored by TLC (silica gel, CHCl$_3$:MeOH:HOAc=8:2:0.2). A solution of 2 M HCl (1.4 mL, 2.8 mmol) was added and the solvent was evaporated under reduced pressure. The residue was taken up in 50 mL CHCl$_3$. After removal of the precipitate, the CHCl$_3$ was removed in vacuo. The residue was triturated in EtOAc to obtain the product as a white solid (0.38 g): mp 130–139° C.; yield, 80%; $^1$H NMR (DMSO-d$_6$) δ 5.0 (m, 3H), 6.7 (m, 1H), 7.0–7.4 (m, 10H), 7.5 (m, 4H), 7.7–7.8 (m, 2H), 8.3 (s, 2H), 9.5 (s, 1H); MS (FAB$^+$) m/z 440.1 (M+H)$^+$. Anal. (C$_{22}$H$_{25}$O$_5$N$_3$P.HCl.0.6H$_2$O) C, H, N.

Cbz-(4-AmPhGly)$^P$(OPh)(OH) can be converted into Cbz-(4-AmPhGly)$^P$(OPh)(F) by reaction with SOCl$_2$ to give the chloro derivative followed by treatment with KF.

EXAMPLE 30

Diphenyl 1-(N-(2-Phenoxybenzoylprolyl)amino)-5-aminopentanephosphonate Hydrochloride {(2-Phenoxybenzoyl-Pro-Lys$^P$(OPh)$_2$}. This product was prepared by general procedure C. The final product was obtained as a white solid containing a small amount of N$_2$H$_4$.HCl as a byproduct: mp 87–89° C.; yield, 93%; $^1$H NMR (DMSO-d$_6$) δ 1.3–2.0 (m, 10H), 2.7 (m, 2H), 3.4 (m, 2H), 4.4–4.6 (m, 3H), 7.0–7.5 (m, 19H), 7.7–7.9 (br s, 3H); HRMS (FAB$^+$) m/z calcd. for C$_{35}$H$_{39}$N$_3$O$_6$P (M+H)$^+$ 628.2576, found 628.2652; HPLC (90% CH$_3$CN/H$_2$O and 10% CH$_3$CN/H$_2$O) major peak (>90%) with several byproducts, t$_R$=12.8 min. Anal. (C$_{35}$H$_{38}$N$_3$O$_6$P.1.3HCl.0.4H$_2$O.0.3N$_2$H$_4$) C, H, N.

EXAMPLE 31

Diphenyl 1-(N-(3-Phenoxybenzoylprolyl)amino)-5-aminopentanephosphonate Hydrochloride {(3-Phenoxybenzoyl)-Pro-Lys$^P$(OPh)$_2$}. This product was prepared by general procedure C. The final product was obtained as a white solid containing a small amount of N$_2$H$_4$.HCl as a byproduct: mp 85–87° C.; yield, 91%; $^1$H NMR (DMSO-d$_6$) δ 1.3–2.1 (m, 10H), 2.7(m, 2H) 3.4 (m, 2H), 4.4–4.6 (m, 3H), 7.0–7.5 (m, 19H), 7.7–7.9 (br s, 3H); HRMS (FAB$^+$) m/z calcd. for C$_{35}$H$_{39}$N$_3$O$_6$P (M+H)$^+$ 626.2576, found 628.2515; HPLC (90% CH$_3$CN/H$_2$O and 10% CH$_3$CN/H$_2$O) major peak (>90%) with several byproducts, t$_R$=13.2 min. Anal. (C$_{35}$H$_{38}$N$_3$O$_6$P.1.2HCl.H$_2$O.0.2N$_2$H$_4$) C, H, N.

EXAMPLE 32

Diphenyl 1-(N-(2-Phenoxybenzoylprolyl)amino)-6-aminohexanephosphonate Hydrochloride {(2-Phenoxybenzoyl)-Pro-HomoLys$^P$(OPh)$_2$}. This product was prepared by general procedure C. The final product was obtained as a white solid containing a small amount of N$_2$H$_4$.HCl as a byproduct: mp 83–85° C.; yield, 42%; $^1$H NMR (DMSO-d$_6$) δ 1.2–2.0 (m, 12H), 2.7 (m, 2H), 3.5 (m, 2H), 4.2–4.7 (m, 2H), 6.9–7.5 (m, 21H), 7.7–7.9 (br s, 3H); HRMS (FAB$^+$) m/z calcd. for C$_{36}$H$_{41}$N$_3$O$_6$P (M+H)$^+$ 642.2733, found 642.2727; HPLC (90% CH$_3$CN/H$_2$O and 10% CH$_3$CN/H$_2$O) two major peaks (diastereomers, 1:0.3) with a trace of byproducts (<5%), t$_R$=12.8, 13.0 min. Anal. (C$_{36}$H$_{40}$N$_3$O$_6$P.1.3HCl.0.4H$_2$O.0.3N$_2$H$_4$) C, H, N.

EXAMPLE 33

Diphenyl 1-(N-(3-Phenoxybenzoylprolyl)amino)-6-aminohexanephosphonate Hydrochloride {(3-Phenoxybenzoyl)-Pro-HomoLys$^P$(OPh)$_2$}. This product was prepared by general procedure C. The final product was obtained as a white solid containing a small amount of N$_2$H$_4$.HCl as a byproduct: mp 79–84° C.; yield, 38%; $^1$H NMR (DMSO-d$_6$) δ 1.1–1.9 (m, 12H), 2.7 (br s, 2H), 3.4–3.6 (m, 2H), 4.2–4.6 (m, 2H), 7.0–7.5 (m, 21H), 7.9 (br s, 3H); HRMS (FAB⁺) m/z calcd. for $C_{36}H_{41}N_3O_6P$ (M+H)⁺ 642.2733, found 642.2768; HPLC (90% $CH_3CN/H_2O$ and 10% $CH_3CN/H_2O$) two major peaks (diastereomers, 1:0.5) with several byproducts (<10%), $t_R$=11.6, 13.6 min. Anal. ($C_{36}H_{40}N_3O_6P \cdot 1.3HCl \cdot 0.5H_2O \cdot 0.3N_2H_4$) C, H, N.

It is obvious that those skilled in the art may make modifications to the invention without departing from the spirit of the invention or the scope of the subjoined claims and their equivalents.

TABLE I

Inhibition of Trypsin-like Serine Proteases by 4-Amidinophenylglycine Phosphonate Diphenyl Ester Derivatives[a]

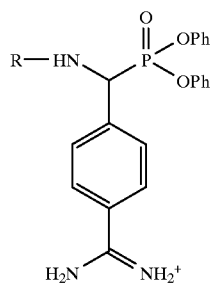

| R = | human granzyme A | rat granzyme A | rat granzyme K | mast cell tryptase | bovine trypsin |
|---|---|---|---|---|---|
| | | | $k_{obsd}/[I]$ (M⁻¹s⁻¹) | | |
| Cbz | 1180 | | 3.8 ± 0.7 | 0.6 | 2000 |
| Suc | 857 | | 0.3 ± 0.07 | 0.2 | 45 ± 3 |
| trans-Cinnamoyl | 400 ± 10 | 340 ± 18 | 3 | 0.3 | 110 ± 1 |
| 3-(2-Furyl)acryloyl | 1740 ± 41 | 1740 ± 237 | 32 | NI[b] | 360 ± 28 |
| 3-(2-Thienyl)acryloyl | 740 ± 18 | 430 ± 31 | 4 | 1 | 300 ± 22 |
| trans-3-(3-Pyridyl)acryloyl | 5 | 1 | 3 | NI | NI[d] |
| 3-Phenoxybenzoyl | 340 ± 53 | 470 ± 14 | 1 | NI | 50 ± 2 |
| 2-Phenoxybenzoyl | 540 ± 3 | 340 ± 1 | 1 | 0.4 | 670 ± 53 |
| 1-NpSO₂ | 330 ± 26 | 30 ± 1 | NI | 10 | 170 ± 34 |
| 1-Naphthylmethoxycarbonyl | 160 ± 2 | 90 ± 9 | 12 | NI | 30 ± 1 |
| Cbz—Ala | 1670 ± 11 | 1270 ± 85 | NI | 0.8 | 1850 ± 85 |
| Cbz—Val | 6.7 ± 0.1 | | 0.7 ± 0.04 | 21.2 ± 0.2 | 41 ± 3 |
| Cbz—Leu | 6.3 ± 0.7 | | NI | 0.3 | 50 ± 1 |
| Cbz—Pro | 790 ± 17 | | 34 ± 4 | 1.2 | 910 ± 81 |
| Cbz—Thr | 2220 ± 40 | | 3 | NI | 97 |
| Cbz—Lys | 30 ± 1 | 15 ± 1 | 1 | NI | 30 ± 1 |
| Cbz—Phe | 14 ± 1 | 8 | 13 | 5% Inh | 17 ± 1 |
| (2-Phenoxybenzoyl)-Pro | 610 ± 88 | | 60 ± 5 | 0.9 | 7760 ± 310 |
| (3-Phenoxybenzoyl)-Pro | 330 ± 58 | | NI | 7% Inh | 4080 ± 32 |
| (3,3-Diphenylpropanoyl)-Pro | 250 ± 8 | | 1830 ± 140 | NI | 2660 ± 40 |
| (3-Phenylpropanoyl)-Pro | 1510 ± 217 | | 50 ± 2 | 0.4 | 1520 ± 27 |
| Cbz—Ala—Ala | 820 ± 29 | 480 ± 27 | 5 | 2 | 3620 ± 588 |
| Suc—Ala—Ala | 260 ± 15 | | 0.3 ± 0.01 | 0.7 | 640 ± 36 |
| Cbz—Pro—Ala | 380 ± 18 | | 5 | 1 | 240 ± 10 |
| Cbz—Asp—Ala | 240 ± 5 | | 6 | 0.7 | 2550 ± 145 |
| Cbz—Asp(t-Bu)—Ala | 280 ± 5 | | NI | 3 | 2000 ± 24 |
| Cbz—Lys—Ala | 90 ± 9 | | NI | 2 | 3140 ± 262 |
| Cbz—Lys(Boc)—Ala | 110 ± 5 | | NI | 8.5 ± 0.4 | 3100 ± 177 |
| Cbz—Phe—Ala | 1770 ± 13 | | 4.2 ± 0.3 | 4 | 3010 ± 318 |
| Boc—D—Phe—Pro | 170 | | 56 ± 2 | 0.4 | 130[b] |
| Ph—CH₂—SO₂—Gly—Pro | 3650 ± 180 | | 87 | 2 | 37060 ± 986 |
| Cbz—Ala—Ala—Ala | 730 ± 15 | 590 ± 17 | 7 | 2 | 1780 ± 33 |

[a]Inhibition constants were measured in 0.1M Hepes, 0.01M CaCl₂, pH 7.5 for trypsin, granzymes A, and K, and in 0.1M Hepes, 10% glycerol, 10 mM heparin, pH 7.5 for mast cell tryptase, and at 25° C. The reaction mixtures contained 2% DMSO for trypsin, 7.6% for granzyme A, and 7.1% for granzyme K and tryptase. The substrate was Z—Arg—SBzl for granzymes and trypsin, and Z—Arg—SBzl or Z—Lys—SBzl for tryptase in the presence of DTNB. The inhibitor concentration ranged from 0.001 to 100 μM.
[b]NI, no inhibition after 25 min of incubation with enzyme.

TABLE II

Inhibition of Thrombin and Other Trypsin-like Enzymes by Derivatives of (4-AmPhGly)$^P$(OPh)$_2$[a]

| | $k_{obs}/[I]$ (M$^{-1}$s$^{-1}$) | | | |
|---|---|---|---|---|
| Inhibitor | human thrombin | bovine trypsin | mast cell tryptase | factor Xa |
| Cbz-(4-AmPhGly)$^P$(OPh)$_2$ | 80[b] | 170[b] | 0.6 | |
| Cbz-(3-AmPhGly)$^P$(OPh)$_2$ | 50% Inh | NI | NI | |
| Cbz-(4-AmPhGly)$^P$(OPh-p-Cl)$_2$ | 9,300 ± 210 | 41,100 ± 5400 | 3 ± 0 | |
| Cbz-(4-AmPhGly)$^P$(OPh)(OMe) | 41 | 83 | | |
| Cbz-(4-AmPhGly)$^P$(OPh)(OH) | NI | 0.3 | NI | |
| Suc-(4-AmPhGly)$^P$(OPh)$_2$ | 2 | 45 ± 3 | 0.2 | |
| trans-Cinnamoyl-(4-AmPhGly)$^P$(OPh)$_2$ | 20 ± 1 | 110 ± 1 | 0.3 | |
| (2-Furyl)acryloyl-(4-AmPhGly)$^P$(OPh)$_2$ | 15 ± 1 | 360 ± 28 | NI | |
| 3-(2-Thienyl)acryloyl-(4-AmPhGly)$^P$(OPh)$_2$ | 90 ± 4 | 300 ± 22 | 1 | |
| 3-(3-Pyridyl)acryloyl-(4-AmPhGly)$^P$(OPh)$_2$ | 2 | NI | NI | |
| 4-Phenylbutanoyl-(4-AmPhGly)$^P$(OPh)$_2$ | 17 ± 1 | 15% Inh | | |
| 2-Phenoxybenzoyl-(4-AmPhGly)$^P$(OPh)$_2$ | 270 ± 20 | 670 ± 53 | 0.4 | |
| 3-Phenoxybenzoyl-(4-AmPhGly)$^P$(OPh)$_2$ | 200 ± 8 | 50 ± 2 | NI | |
| 1-Naphthyloxycarbonyl-(4-AmPhGly)$^P$(OPh)$_2$ | 30 ± 2 | 30 ± 1 | NI | |
| Tolyl-SO$_2$-(4-AmPhGly)$^P$(OPh)$_2$ | 94 ± 26 | 35 ± 6 | | |
| 1-NpSO$_2$-(4-AmPhGly)$^P$(OPh)$_2$ | 24 ± 3 | 170 ± 34 | 10 ± 1 | |
| Cbz—Gly-(4-AmPhGly)$^P$(OPh)$_2$ | 24 ± 3 | 195 ± 9 | | |
| Cbz—Ala-(4-AmPhGly)$^P$(OPh)$_2$ | 750 ± 18 | 1,850 ± 85 | 0.8 | |
| Cbz—Val-(4-AmPhGly)$^P$(OPh)$_2$ | 5.5 ± 0.4 | 18 ± 2 | 21.2 ± 0.2 | |
| Cbz—Leu-(4-AmPhGly)$^P$(OPh)$_2$ | 19% Inh | 1.3 ± 0.1 | 0.3 | |
| Boc—Ser-(4-AmPhGly)$^P$(OPh)$_2$ | 31 ± 2 | 20 ± 1 | | 3.5 ± 0.4 |
| Cbz—Thr-(4-AmPhGly)$^P$(OPh)$_2$ | 61 ± 3 | 97 ± 2 | NI | |
| Cbz—Lys-(4-AmPhGly)$^P$(OPh)$_2$ | 88 ± 2 | 30 ± 1 | NI | |
| Cbz—Phe-(4-AmPhGly)$^P$(OPh)$_2$ | 20 ± 1 | 17 ± 1 | 5% Inh | |
| Cbz—Trp-(4-AmPhGly)$^P$(OPh)$_2$ | 1.2 ± 0.0 | 0.6 | | |
| Cbz—Pro-(4-AmPhGly)$^P$(OPh)$_2$ | 640 ± 86 | 910 ± 81 | 1 | |
| 2-Phenoxybenzoyl-Pro-(4-AmPhGly)$^P$(OPh)$_2$ | 42,400 ± 4190 | 7,760 ± 310 | 0.9 | |
| 3-Phenoxybenzoyl-Pro-(4-AmPhGly)$^P$(OPh)$_2$ | 1,340 ± 225 | 4,080 ± 32 | 7% Inh | |
| 3-Phenylpropanoyl-Pro-(4-AmPhGly)$^P$(OPh)$_2$ | 6,070 ± 68 | 1,520 ± 27 | 0.4 | |
| 3,3-Diphenylpropanoyl-Pro-(4-AmPhGly)$^P$(OPh)$_2$ | 80,300 ± 368 | 2,660 ± 40 | NI | |
| Boc—D—Leu—Gly-(4-AmPhGly)$^P$(OPh)$_2$ | 1,187 ± 76 | 2,960 ± 300 | | 10 ± 0.4 |
| Boc—D—Phe—Gly-(4-AmPhGly)$^P$(OPh)$_2$ | 2,225 ± 106 | 6,620 ± 835 | | 2.8 ± 0 |
| Cbz—Glu—Gly-(4-AmPhGly)$^P$(OPh)$_2$ | 46 ± 5 | 70 ± 5 | | 1.4 ± 0.1 |
| Cbz—Ala—Ala-(4-AmPhGly)$^P$(OPh)$_2$ | 3,030 ± 222 | 3,620 ± 588 | 2 ± 0 | |
| Suc—Ala—Ala-(4-AmPhGly)$^P$(OPh)$_2$ | 2 | 640 ± 36 | 0.7 | |
| Cbz—Pro—Ala-(4-AmPhGly)$^P$(OPh)$_2$ | 70 ± 2 | 240 ± 10 | 1 ± 0 | |
| Cbz—Asp—Ala-(4-AmPhGly)$^P$(OPh)$_2$ | 110 ± 12 | 2,550 ± 145 | | |
| Cbz—Asp(O-t-Bu)—Ala-(4-AmPhGly)$^P$(OPh)$_2$ | 480 ± 93 | 2,000 ± 24 | 3 ± 0 | |
| Cbz—Lys—Ala-(4-AmPhGly)$^P$(OPh)$_2$ | 180 ± 7 | 3,140 ± 262 | 2.0 ± 0.0 | |
| Cbz—Lyz(Boc)—Ala-(4-AmPhGly)$^P$(OPh)$_2$ | 450 ± 58 | 3,100 ± 177 | 8.7 ± 0.4 | |
| Cbz—Phe—Ala-(4-AmPhGly)$^P$(OPh)$_2$ | 1,150 ± 88 | 3,010 ± 318 | 4.0 ± 0.3 | |
| Boc—Val—Val-(4-AmPhGly)$^P$(OPh)$_2$ | 85 ± 5 | 61 ± 5 | | |
| Boc—D—Phe—Val-(4-AmPhGly)$^P$(OPh)$_2$ | 63 ± 4 | 30 ± 2 | | |
| Boc—D—Phe—Leu-(4-AmPhGly)$^P$(OPh)$_2$ | 921 ± 44 | 24 ± 2 | | 1.4 ± 0.4 |
| Boc—Leu—Ser-(4-AmPhGly)$^P$(OPh)$_2$ | 97 ± 2 | 177 ± 2 | | |
| Boc—D—Phe—Pro-(4-AmPhGly)$^P$(OPh)$_2$[b] | 11,000 | 2,200 | | |
| PhCH$_2$SO$_2$—Gly—Pro-(4-AmPhGly)$^P$(OPh)$_2$ | 17,200 ± 128 | 37,060 ± 986 | 2.0 ± 0.1 | |
| Leu—Thr-(4-AmPhGly)$^P$(OPh)$_2$ | 58 ± 3 | 24.5 ± 0.0 | | |
| Boc—Leu—Thr-(4-AmPhGly)$^P$(OPh)$_2$ | 75 ± 1 | 35 ± 6 | | |
| Cbz—Ala—Ala—Ala-(4-AmPhGly)$^P$(OPh)$_2$ | 1,290 ± 26 | 1,780 ± 33 | 2.0 ± 0.2 | |
| Leu—Asp—Pro-(4-AmPhGly)$^P$(OPh)$_2$ | 65 ± 1 | 204 ± 19 | | 1.3 ± 0.2 |
| Boc—Leu—Asp(O-t-Bu)—Pro-(4-AmPhGly)$^P$(OPh)$_2$ | 502 ± 21 | 670 ± 53 | | 8 ± 1 |
| Boc—Asn—Leu—Thr-(4-AmPhGly)$^P$(OPh)$_2$ | 46 ± 6 | 18 ± 2 | | |

[a]Enzyme was incubated with the inhibitor in 250 μL of the proper buffer at 25° C. Specifically, the inhibition reation mixtures were composed of: 0.13 μM trypsin, 0.25–42 μM inhibitor in an 80 mM Hepes, pH 7.5 buffer containing 1 mM CaCl$_2$ and 8% DMSO; 0.07 μM thrombin, 0.25–42 μM inhibitor in an 80 mM Hepes, pH 7.5 buffer containing 428 mM NaCl and 8% DMSO; 0.07 μM tryptase, 20–66 μM inhibitor in an mM Hepes, pH 7.5 buffer containing 8 mM heparin, 166 mM NaCl, 0.8 mM Mes, 9% glycerol and 8% DMSO; 0.42 μM factor Xa, 66 μM inhibitor in an 80 mM Hepes, pH 7.5 buffer containing 428 mM NaCl and 8% DMSO. Aliquots of 25 μL were withdrawn at various intervals and the residual enzymatic activity was measured as described in experimental section. The $k_{obs}$ values were calculated from pseudo-first-order plots.

TABLE III

Inhibition of Thrombin and Other Trypsin-like Enzymes by Derivatives of Lysine Phosphonates[a]

| Inhibitor | human thrombin | bovine trypsin | plasmin | urokinase | mast cell tryptase |
|---|---|---|---|---|---|
| Cbz—Orn$^P$(OPh)$_2$ | NI | NI | NI | NI | NI |
| Cbz—Lys$^P$(OPh)$_2$ | 17 | 6,235 | 8.2 ± 0.4 | 15 ± 2 | 17 ± 1 |
| 2-Phenoxybenzoyl-Pro—Lys$^P$(OPh)$_2$ | 4,531 ± 140 | 16,411 ± 460 | 7.1 ± 0.2 | 0.6 ± 0.1 | 19 ± 1 |
| 3-Phenoxybenzoyl-Pro—Lys$^P$(OPh)$_2$ | 1,142 ± 52 | 19,380 ± 300 | 7.4 ± 0.6 | 1.6 ± 0.1 | 16 ± 1 |
| 3,3-Diphenylpropanoyl-Pro—Lys$^P$(OPh)$_2$ | 27,450 ± 803 | 14,447 ± 905 | 7.0 ± 0.2 | 1.5 ± 0.0 | 74 ± 9 |
| Cbz—Thr—Lys$^P$(OPh)$_2$ | NI | 230 | | 0.7 ± 0.1 | 7 ± 1 |
| Boc—Asn—Lys$^P$(OPh)$_2$ | NI | 3 | | NI | NI |
| Boc—Lys(Cbz)—Lys$^P$(OPh)$_2$ | NI | NI | | NI | NI |
| Boc—D—Phe—Pro—Lys$^P$(OPh)$_2$ | 9,364 ± 110 | 28,840 ± 1,800 | 51 ± 4 | 38 ± 3 | 68 ± 4 |
| Suc—Val—Pro—Lys$^P$(OPh)$_2$ | 3.4 ± 0.4 | 416 ± 28 | | NI | 0.6 |
| PhCH$_2$SO$_2$—Gly—Pro—Lys$^P$(OPh)$_2$ | 649 ± 14 | 12,472 ± 1,400 | 13 ± 1 | 39 ± 2 | 24 ± 0 |
| Cbz-HomoLys$^P$(OPh)$_2$ | NI | 21 ± 6 | NI | 1.0 ± 0.0 | 0.7 |
| 2-Phenoxybenzoyl-Pro-HomoLys$^P$(OPh)$_2$ | 57 ± 5 | 69 ± 13 | 3.6 ± 0.4 | 24 ± 4 | 7.7 ± 0.3 |
| 3-Phenoxybenzoyl-Pro-HomoLys$^P$(OPh)$_2$ | 27 ± 5 | 116 ± 34 | 4.6 ± 0.1 | 22 ± 1 | 10 ± 3 |
| 3,3-Diphenylpropanoyl-Pro-HomoLys$^P$(OPh)$_2$ | 224 ± 8 | 16 ± 1 | 50% Inh[b] | 2.1 ± 0.2 | 1.1 ± 0.0 |
| D—Phe—Pro-HomoLys$^P$(OPh)$_2$ | 1,342 ± 272 | 164 ± 14 | NI | 7.8 ± 0.0 | 4.1 0.2 |
| Suc—Val—Pro-HomoLys$^P$(OPh)$_2$ | 1.6 ± 0.3 | 51 ± 10 | NI | NI | 4.1 ± 0.4 |
| PhCH$_2$SO$_2$Gly—Pro-HomoLys$^P$(OPh)$_2$ | 137 ± 12 | 528 ± 59 | 8.4 ± 0.2 | 38 ± 3 | 32 ± 2 |

[a]Enzyme (0.06–0.5 μM) was incubated with the inhibitor (0.25–42 μM) in 250 μL of the proper buffer containing 9% DMSO at 25° C. The final inhibition reaction mixtures are given in the footnote to Table 1. Aliquots of 25 μL were withdrawn at various intervals and the residual enzymatic activity was measured as described in experimental section. The $k_{obs}$ values were calculated from pseudo-first-order plots.
[b]Inhibitor concentration of 0.24 mM.

What is claimed is:

1. A compound of the formula:

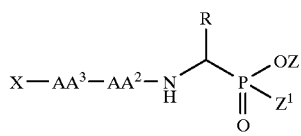

or a pharmaceutically acceptable salt thereof, wherein:

R is selected from the group consisting of phenyl substituted with B, benzyl substituted with B on the phenyl ring, and $C_{1-6}$ alkyl substituted with B, B is selected from the group consisting of amidino {—C(=NH)NH$_2$}, guanidino {—NH—C(=NH)NH$_2$}, isothiureido {—S—C(=NH)NH$_2$}, and amino, Z is selected from the group consisting of $C_{1-6}$ perfluoroalkyl, phenyl, phenyl monosubstituted with J, phenyl disubstituted with J, and phenyl trisubstituted with J, $Z^1$ is selected from the group consisting of $C_{1-6}$ perfluoroalkoxy, phenoxy, phenoxy monosubstituted with J, phenoxy disubstituted with J, phenoxy trisubstituted with J, $C_{1-6}$ alkoxy, and halogen, J is selected from the group consisting of halogen, $C_{1-6}$ alkyl, $C_{1-6}$ perfluoroalkyl, $C_{1-6}$ alkoxy, NO$_2$, CN, OH, CO$_2$H amino, $C_{1-6}$ alkylamino, $C_{2-12}$ dialkylamino, $C_{1-6}$ acyl, $C_{1-6}$ alkoxy-CO—, and $C_{1-6}$ alkyl-S—, AA$^3$ and AA$^2$ are the same or different and are selected from the group consisting of (a) a single bond, and (b) a blocked or unblocked amino acid residue with the L or D configuration at the α-carbon carbon selected from the group consisting of alanine, valine, leucine, isoleucine, proline, methionine, methionine sulfoxide, phenylalanine, tryptophan, serine, threonine, cysteine, tyrosine, asparagine, glutamine, aspartic acid, glutamic acid, lysine, arginine, histidine, phenylglycine, norleucine, norvaline, alpha-aminobutyric acid, citrulline, hydroxyproline, ornithine, homolysine, and homoarginine, and (c) glycine, sarcosine, epsilon-aminocaproic acid, and beta-alanine, X is selected from the group consisting of Y—CO— and Y—SO$_2$—, Y is selected from the group consisting of (a) C$_6$H$_5$—CH=CH—, (2-furyl)-CH=CH—, (2-thienyl)-CH=CH—, and (2-pyridyl)—CH=CH—, (b) $C_{1-6}$ alkenyl substituted with a heterocyclic group, (c) $C_{1-6}$ alkenyl substituted with a moiety selected from the group consisting of phenyl, phenyl monosubstituted with K, phenyl disubstituted with K, phenyl trisubstituted with K, naphthyl, naphthyl monosubstituted with K, naphthyl disubstituted with K, and naphthyl trisubstituted with K, (d) 2-phenoxyphenyl and 3-phenoxyphenyl, (e) Phenyl substituted with a moiety selected from the group consisting of phenoxy, phenoxy monosubstituted with K, phenoxy disubstituted with K, phenoxy trisubstituted with K, naphthyloxy, naphthyloxy monosubstituted with K, naphthyloxy disubstituted with K, and naphthyloxy trisubstituted with K, and K is selected from the group consisting of halogen, $C_{1-6}$ alkyl, $C_{1-6}$ perfluoroalkyl, $C_{1-6}$ alkoxy, NO$_2$, CO$_2$H, amino, $C_{1-6}$ alkylamino, $C_{2-12}$ dialkylamino, $C_{1-6}$ acyl, $C_{1-6}$ alkoxy-CO—, and $C_{1-6}$ alkyl-S—.

2. A compound according to claim 1 wherein R is selected from the group consisting of (a) 3-amidinophenyl, (b) 4-amidinophenyl, (c) 3-amidinobenzyl, (d) 4-amidinobenzyl, (e) 3-guanidinophenyl, (f) 4-guanidinophenyl, (g) 3-guanidinobenzyl, and (h) 4-guanidinobenzyl.

3. A compound according to claim 2 wherein

AA$^2$ is an amino acid residue selected from the group consisting of alanine, glycine, isoleucine, leucine, proline, phenylalanine, threonine, serine, and valine, AA$^3$ is selected from the group consisting of (a) a single bond, (b) an amino acid residue selected from the group consisting of alanine, glycine, isoleucine, leucine, plienylalanine, and valine, X is Y—CO—, Y is selected from the group consisting of (a) C$_6$H$_5$—CH=CH—, (2-furyl)-CH=CH—, (2-thienyl)-CH=CH—, and (2-pyridyl)-CH=CH—, (b) $C_{1-6}$ alkenyl substituted with a heterocyclic group, (c) $C_{1-6}$ alkenyl substituted with a moiety selected from the group consisting of phenyl, phenyl monosubstituted with K, phenyl disubstituted with K, phenyl trisubstituted with K, naphthyl, naphthyl monosubstituted with K, naphthyl disubstituted with K, and naphthyl trisubstituted with K, (d) 2-phenoxyphenyl and 3-phenoxyphenyl, (e) Phenyl substituted with a moiety selected from the group consisting of phenoxy, phenoxy monosubstituted with K, phenoxy disubstituted with K, phenoxy trisubstituted with K, naphthyloxy, naphthyloxy monosubstituted with K, naphthyloxy disubstituted with K, and naphthyloxy trisubstituted with K, and K is selected from the group consisting of halogen, $C_{1-6}$ alkyl, $C_{1-6}$ perfluoroalkyl, $C_{1-6}$ alkoxy, NO$_2$, CN, OH, $CO_2H$, amino, $C_{1-6}$ alkylamino, $C_{2-12}$ dialkylamino, $C_{1-6}$ acyl $C_{1-6}$ alkoxy-CO—, and $C_{1-6}$ alkyl-S—.

4. A compound according to claim 1 wherein R is selected from the group consisting of
(a) —$CH_2CH_2CH_2NH$—C(=$NH$)$NH_2$,
(b) —$CH_2CH_2CH_2CH_2NH_2$,
(c) —$CH_2CH_2CH_2NH_2$, and
(d) —$CH_2CH_2CH_2CH_2CH_2NH_2$.

5. A compound according to claim 4 wherein
$AA^2$ is an amino acid residue selected from the group consisting of alanine, glycine, isoleucine, leucine, proline, phenylalanine, threonine, serine, and valine,
$AA^3$ is selected from the group consisting of
(a) a single bond,
(b) an amino acid residue selected from the group consisting of alanine, glycine, isoleucine, leucine, phenylalanine, and valine,
X is Y—CO—,
Y is selected from the group consisting of
(a) $C_6H_5$—CH=CH—, (2-furyl)-CH=CH—, (2-thienyl)-CH=CH—, and (2-pyridyl)-CH=CH—,
(b) $C_{1-6}$ alkenyl substituted with a heterocyclic group,
(c) $C_{1-6}$ alkenyl substituted with a moiety selected from the group consisting of phenyl, phenyl monosubstitued with K, phenyl disubstituted with K, phenyl trisubstituted with K, naphthyl, naphthyl monosubstituted with K, naphthyl disubstituted with K, and naphthyl trisubstituted with K,
(d) 2-phenoxybenzoyl and 3-phenoxybenzoyl,
(e) Phenyl substituted with a moiety selected from the group consisting of phenoxy, phenoxy monosubstituted with K, phenoxy disubstituted with K, phenoxy trisubstituted with K, naphthyloxy, naphthyloxy monosubstituted with K, naphthyloxy disubstituted with K, and naphthyloxy trisubstituted with K, and K is selected from the group consisting of halogen, $C_{1-6}$ alkyl, $C_{1-6}$ perfluoroalkyl, $C_{1-6}$ alkoxy, $NO_2$, CN, OH, $CO_2H$, amino, $C_{1-6}$ alkylamino, $C_{2-12}$ dialkylamino, $C_{1-6}$ acyl, $C_{1-6}$ alkoxy-CO—, and $C_{1-6}$ alkyl-S—.

6. A compound selected from the group consisting of:
(a) Cinnamoyl-(4-AmPhGly)$^P$(OPh)$_2$,
(b) 3-(2-Furyl)acryloyl-(4-AmPhGly)$^P$(OPh)$_2$,
(c) 3-(3-Thienyl)acryloyl-(4-AmPhGly)$^P$(OPh)$_2$,
(d) 3-(2-Pyridyl)acryloyl-(4-AmPhGly)$^P$(OPh)$_2$,
(e) 2-Phenoxybenzoyl-(4-AmPhGly)$^P$(OPh)$_2$,
(f) 3-Phenoxybenzoyl-(4-AmPhGly)$^P$(OPh)$_2$,
(g) 2-Phenoxybenzoyl-Pro-(4-AmPhGly)$^P$(OPh)$_2$,
(h) 3-Phenoxybenzoyl-Pro-(4-AmPhGly)$^P$(OPh)$_2$,
(i) 2-Phenoxybenzoyl-Pro-Lys$^P$(OPh)$_2$,
(j) 3-Phenoxybenzoyl-Pro-Lys$^P$(OPh)$_2$,
(k) 2-Phenoxybenzoyl-Pro-HomoLys$^P$(OPh)$_2$, and
(l) 3-Phenoxybenzoyl-Pro-HomoLys$^P$(OPh)$_2$.

7. A process for inhibiting serine protease activity comprising the step of adding to a medium containing the protease that amount of the compound of claim 1 effective to inhibit said activity.

8. A method of decreasing blood coagulation comprising the administration to a mammalian species in need of such treatment a therapeutically effective amount of the compound of claim 1.

* * * * *